US005908749A

United States Patent [19]
Mignot et al.

[11] Patent Number: 5,908,749
[45] Date of Patent: Jun. 1, 1999

[54] METHODS AND COMPOSITIONS FOR HIGH RESOLUTION HLA TYPING

[75] Inventors: Emmanuel J. M. Mignot, Palo Alto, Calif.; Claudia I. P. Macaubas, North Perth, Australia; Li Jin, Houston, Tex.; Lin Ling, Mountain View, Calif.

[73] Assignee: TGE Board of Trustees of the Leland Stanford Junior University, Palo Alto, Calif.

[21] Appl. No.: 08/829,961

[22] Filed: Apr. 1, 1997

Related U.S. Application Data

[63] Continuation-in-part of application No. 08/391,374, Feb. 17, 1995, abandoned.

[51] Int. Cl.[6] .............................. C12Q 1/68; C12P 19/34; C07H 19/00; C07H 21/04
[52] U.S. Cl. .......................... 435/6; 435/91.2; 536/22.1; 536/24.31; 536/24.33
[58] Field of Search ................... 435/6, 91.2; 536/24.31, 536/24.33; 935/6, 17, 77, 78

[56] References Cited

U.S. PATENT DOCUMENTS

| 4,683,195 | 7/1987 | Mullis et al. ................................ 435/6 |
| 5,192,659 | 3/1993 | Simons ........................................ 435/6 |
| 5,310,893 | 5/1994 | Erlich et al. ........................... 536/24.31 |
| 5,364,759 | 11/1994 | Caskey et al. .............................. 435/6 |
| 5,468,611 | 11/1995 | Baxter-Lowe et al. ...................... 435/6 |
| 5,582,979 | 12/1996 | Weber ........................................ 435/6 |

OTHER PUBLICATIONS

Fullan et al (1994). A polymorphic dinucleotide repeat at the human HLA–F locus, Dec. 1994.
Carpenter. Tissue Antigens 30:322–325 Oct. 1997.
Chatkupt et al. Am. J. Med. Genet. 52:1–4 Aug. 1994.
Elder et al. J. Investigative Dermatology 102:248–275 Jun. 1994.
Nepom et al., "MHC Class–II Molecules and Autoimmunity," *Annu. Rev. Immunol.* 9:493–525 (1991).
Sinha et al., "Autoimmune Diseases: The Failure of Self Tolerance," *Science* 248:1380–1388 (1990).
Imanishi et al., "Estimation of Allele and Haplotype Frequencies for HLA and Complement Loci," HLA 1991 Proceedings of the Eleventh International Histocompatibility Workshop and Conference Held in Yokohama, Japan, vol. One, pp. 76–79 (Nov. 6–13, 1991).
"A Comprehensive Genetic Linkage Map of the Human Genome," *Science* 258:67–86 (1992).
Jin et al., "Tracking the Evolutionary History of a Microsatellite Locus Located in the HLA–DQA1/DQB1 Class II Region: A Phylogenetic Approach," *Current Topics on Molecular Evolution* (1995).
Mignot et al., "DQCAR Microsatellite Polymorphisms in Three Seleted HLA Class II–Associated Diseases," *Tissue Antigens* (1995).
Cullen et al., "Characterization of Recombination in HLA Class II Region," *Am. J. Hum. Genet.* (1997).
Reveille et al., "Association of Polar Amino Acids at Position 26 of the HLA–DQB1 First Domain with the Anticentromere Autoantibody Response in Systemic Sclerosis (Scleroderma)," *The Journal of Clinical Investigation* (1992).

(List continued on next page.)

*Primary Examiner*—Carla J. Myers
*Assistant Examiner*—Diana Johannsen
*Attorney, Agent, or Firm*—Arnold, White & Durkee

[57] ABSTRACT

Methods and compositions are provided for high resolution HLA typing using microsatellite repeats in the HLA region of the genome. Alleles from these markers are shown to be in tight linkage disequilibrium with HLA-DQ/DR alleles. The methods can be carried out on amplified nucleic acid produced by the polymerase chain reaction using the novel primers of the present invention. The microsatellite marker characterization may be employed in the association of diseases to HLA. The typing methods may be further employed in determining the suitability of a donor for tissue transplantation, including bone marrow transplantation, and in determining an individual's susceptibility to HLA associated diseases, particularly autoimmune diseases.

17 Claims, 5 Drawing Sheets

OTHER PUBLICATIONS

Imanishi et al., "Genetic Relationships Among Various Human Populations Indicated by MHC Polymorphisms," *HLA 1991 Proceedings of the Eleventh International Histocompatibility Workshop and Conference Held in Yokohama, Japan,* vol. One, pp. 627–632 (Nov. 6–13, 1991).

Satyanarayana et al., "DNA Sequences Near a Meiotic Recombinational Breakpoint Within the Human HLA–DQ Region," *Immunogenetics* 35:235–240 (1992).

Blanck et al., "Molecular Organization of the DQ Subregion (DO–DX–DV–DQ) of the Human MHC and its Evolutionary Implications," *Journal of Immunology* 141;1734–1737 (1988).

Fernandez–Vina et al., "Alleles at Four HLA Class II Loci Determined by Oligonucleotide Hybridization and their Associations in Five Ethnic Groups," *Immunogenetics* 34:299–312 (1991).

Olerup et al., "HLA–DQB1 and –DQA1 Typing by PCR Amplification with Sequence–Specific Primers (PCR–SSP) in 2 Hours," *Tissue Antigens* 41:119–134 (1993).

Yang et al., "Description of the Reference Panel of B–Lymphoblastoid Cell Lines for Factors of the HLA System: The B–Cell Line Panel Designed for the Tenth International Histocompatibility Workshop," *Immunobiology of HLA* 1:11–19 (1989).

```
          +10        +20        +30        +40        +50
1   TCTAGAAACA TATATTAACA GAGACAGACA AACACACACA CACACACACA
    ------------------------------------>
51  CACACACACA CACACACACA CACACAGCAA GAGAGAGAGA TGAGATAATA

101 TATGAAGTGA TAAGGAAGAG AAATGCAGAA AAAATAGACG CAAAAGAACA
    <-----------------------------
151 CGAGATAGAA AAAATGCAGA TAAACAG
```

FIG. 1

METHODS AND COMPOSITIONS FOR HIGH RESOLUTION HLA TYPING

This is a continuation-in-part application of application Ser. No. 08/391,374 entitled, "Methods and Compositions for Characterizing and Typing a Polymorphic DQCAR Microsatellite Marker," filed Feb. 17, 1995, now abandoned.

The government may own certain rights in the present invention pursuant to National Institutes of Health grants P01-2734 and HL-11383.

FIELD OF THE INVENTION

This invention relates generally to methods and compositions for high resolution HLA typing using polymorphic microsatellite markers in the HLA region of human genomic DNA. The microsatellite markers typically comprise a series of repeating CA units, $(CA)_n$, in the HLA region and provide high resolution typing of this region based upon the association between specific microsatellite alleles and specific HLA types. This invention also relates to novel primers which, in a preferred embodiment, may be used in amplification steps for the methods of the invention. This invention relates generally to the fields of genetics, diagnostic medicine, and tissue and organ transplantation.

BACKGROUND OF THE INVENTION

Genetic susceptibility for more than forty diseases, most of them autoimmune in nature, is associated with genes encoded within the major histocompatibility complex (MHC), particularly the class I (HLA-A, B, C) and class II (Ia, HLA-D) MHC molecules. In many cases, the disease associations are strongest with HLA class II DR and DQ, suggesting that the DR/DQ subregion may be more important than other parts of the HLA region for autoimmunity dysfunction. Due to strong linkage disequilibrium in this genomic region for some populations, it is difficult to determine the specific genes involved in disease susceptibility.

In some cases, this difficulty can be circumvented by studying disease association in various ethnic groups. For example, in African populations, opportunities for ancestral intra-HLA recombinations (crossovers) have been numerous and haplotypic diversity is greater. In these populations, linkage disequilibria between specific HLA-DR and -DQ alleles is often weaker, which can help determine which region (DR or DQ) is more specifically involved in disease susceptibility. In addition, for some autoimmune diseases, complementation of HLA-DQA1 and -DQB1 alleles seems predisposed to disease as strongly as cis located alleles, thus suggesting the involvement of the DQ heterodimer itself rather than HLA-DR or another linked gene. The relatively limited number of haplotypic combinations found in all ethnic groups means that these strategies are not always applicable. Finer analyses of the association between HLA region genes and disease could therefore benefit from the definition of additional polymorphisms in the DR and DQ regions.

Due to their high degree of polymorphism in most mammalian species, microsatellite markers such as the $(CA)_n$ repeats, or GT on the complementary strand, are candidates for use in related gene mapping studies. The $(CA)_n$ repeat sequences are estimated to occur every 30 kb in the haploid human genome. However, such repetitive elements are typically quite unstable, giving rise to very high mutation rates. Because of these high mutation rates, the utility of multialleleic markers for linkage disequilibrium studies has been uncertain. Thus, one would not expect that specific alleles of multiallelic markers would be significantly associated with particular genes.

Although HLA typing provides valuable information regarding disease susceptibility and suitability of tissue/organ transplantation donors, traditional methods of obtaining this information are laborious and expensive. One commonly used approach employs serological evaluation. To do so, HLA class I and II antigens are typed using a complement mediated lymphocytotoxicity test using purified T or B lymphocytes. HLA class I and II specific antisera are purified using naturally immunized individuals, in general multipare women.

Although HLA typing using serological methods to identify class I (A, B, and C) antigens are widely used, DNA-based methods have become more widespread to type HLA class II antigens (DR, DQ, and DP). The most common DNA-based method used is oligotyping. In this method, the polymerase chain reaction (PCR) is combined with dot-blot hybridization with sequence-specific oligonucleotide probes (SSOP) (e.g. forward or reverse dot blotting). PCR-SSP (sequence specific primer) and PCR-SSCP (single strand comformation polymorphism) methods represent other common DNA typing techniques used for HLA typing.

Our co-pending application Ser. No. 08/391,374, now abandoned discloses the unexpected finding that a polymorphic microsatellite marker in the HLA DQ region of the genome gives rise to distinct alleles which are strongly associated with specific HLA DQ alleles. This finding indicates that microsatellite markers in the HLA region can be useful in predicting HLA type. As HLA typing provides valuable information regarding disease susceptibility and suitability of donor tissue for transplantation, microsatellite markers which can predict HLA type are therefore useful in these capacities as well. Additional microsatellite markers from the HLA region are herein disclosed, providing further basis for a novel method of HLA typing which is simple, rapid, and inexpensive relative to traditional HLA typing methods.

SUMMARY OF THE INVENTION

The invention broadly concerns the use of polymorphic microsatellite markers in the HLA region of the human genome for high resolution HLA typing, for evaluating disease susceptibility, and for determining the suitability of donors for tissue or organ transplantation. The invention further relates to methods and compositions for characterizing polymorphic microsatellite markers in the HLA region. The identity and frequency of alleles for the DQCAR, DQCARII and G51152 markers were determined and applied to the testing of various HLA DQ/DR haplotypic combinations. These markers were found to be in tight linkage disequilibrium with HLA DQ. This characterization may be further employed in developing disease associations with HLA.

The invention also relates to methods and compositions for microsatellite HLA typing of individuals using the microsatellite markers of the present invention, or other suitable markers derived from the HLA region of the genome. The invention is further related to a method for determining the suitability of a donor for tissue and organ transplantation, for example, in bone marrow transplantation, which employs microsatellite HLA typing. The invention also relates to a method for detecting an individual's susceptibility to HLA associated diseases, particularly autoimmune disorders, which employs microsatellite HLA typing. The present invention is also directed to the development of such methods which are simpler, faster and less expensive than traditional HLA typing methods.

Thus, in accordance with one aspect of the present invention, there is provided a method of HLA typing, comprising:

(a) characterizing at least one multiallelic microsatellite marker in the HLA region, comprising the steps of
  (i) providing a sample containing DNA;
  (ii) determining the allele length of a multiallelic microsatellite marker in the HLA region of said DNA;
  (iii) determining the HLA type of the sample by oligotyping;
  (iv) repeating steps (i)–(iii) for a statistically significant number of samples; and
  (v) identifying a significant association between microsatellite allele length and HLA type; and
(b) predicting an HLA type of an individual by determining the allele length of the multiallelic microsatellite marker characterized in step (a).

Additionally, the invention relates to novel primers and compositions containing the novel primers. In a preferred embodiment the primers are employed in the methods of the invention to amplify the DQCAR, DQCARII, and G51152 microsatellite markers, for example, by the polymerase chain reaction (PCR).

Preferred primers used to amplify the DQCAR locus, also referred to as CAR1 and CAR2, are identified as the following sequences:

SEQ ID NO. 1: 5' GAAACATATATTAACAGAGACA-GACAAA 3'; and
SEQ ID NO. 2: 5' CATTTCTCTTCCTTATCACTTCATA 3', or nucleic acid sequences complementary to SEQ ID NO. 1 and SEQ ID NO. 2.

Preferred primers used to amplify the DQCARII locus, also referred to as CADQFF and CADQR3, are identified as the following sequences:

SEQ ID NO. 4: 5' TGATTCATAAGGCAAGAATCCAG-CATATTGG 3'; and
SEQ ID NO. 5: 5' GCACTATCATTAAATTTGCTTTC-CACAGTAC 3', or nucleic acid sequences complimentary to SEQ ID NO. 4 and SEQ ID NO. 5.

Preferred primers used to amplify the G51152 locus, also referred to as G51152F and G51152R, are identified as the following sequences:

SEQ ID NO. 6: 5' GGTAAAATTCCTGACTGGCC3'; and
SEQ ID NO. 7: 5' GACAGCTCTTCTTAACCTGC 3', or nucleic acid sequences complimentary to SEQ ID NO. 6 and SEQ ID NO. 7.

The primers of the present invention may also be identified as primers having at least 20 bases, wherein said 20 bases match a series of at least 20 continuous bases within a sequence selected from the group consisting of SEQ ID NO. 1, SEQ ID NO. 2, SEQ ID NO. 4, SEQ ID NO. 5, SEQ ID NO. 6, or SEQ ID NO. 7 or nucleic acid sequences complementary to SEQ ID NO. 1, SEQ ID NO. 2, SEQ ID NO. 4, SEQ ID NO. 5, SEQ ID NO. 6, or SEQ ID NO. 7. Alternatively, under the same definition, the primer may have at least 15 bases or at least (m-5) bases, wherein m is the number of bases in the sequence, e.g., SEQ ID NO. 1, SEQ ID NO. 2, SEQ ID NO. 4, SEQ ID NO. 5, SEQ ID NO. 6, SEQ ID NO. 7 or their complementary sequences. One skilled in the art would understand that, in some cases, a primer sequence may by slightly modified, for example by the number of bases or by deletion, addition, or substitution of bases. Such modified sequences may still be selective for microsatellite typing, but selectivity may be decreased to some extent.

The invention further relates to oligonucleotides of less than about 35–100 bases, more preferably less than about 50 bases or less than about 45 bases, and most preferably less than about 40 or 35 bases, which include a DNA segment of SEQ ID NO. 1, SEQ ID NO. 2, SEQ ID NO. 4, SEQ ID NO. 5, SEQ ID NO. 6, SEQ ID NO. 7, or nucleic acid sequences complementary to SEQ ID NO. 1, SEQ ID NO. 2, SEQ ID NO. 4, SEQ ID NO. 5, SEQ ID NO. 6, or SEQ ID NO. 7. In a preferred embodiment, the oligonucleotide will selectively hybridize to human genomic DNA in the HLA DQ/DR region. One skilled in the art, however, will recognize that the present invention is also applicable to use of microsatellite markers in other HLA regions.

Another embodiment of the invention includes a kit containing two or more primers of SEQ ID NO. 1, SEQ ID NO. 2, SEQ ID NO. 4, SEQ ID NO. 5, SEQ ID NO. 6, or SEQ ID NO. 7 for use in high resolution typing of the HLA DQ/DR region, assessing disease susceptibility, and evaluating the suitability of transplantation donors.

Other and further features and advantages will be apparent and the invention will be more readily understood from a reading of the following specification and by reference to the accompanying drawings, forming a part thereof, where examples of the presently preferred embodiments of the invention are given for the purpose of disclosure.

To aid in understanding the invention, several terms are defined below.

"Microsatellite HLA typing" refers to the use of polymorphic microsatellite markers in the HLA region for high resolution HLA typing. This approach is possible based on the present findings that microsatellite markers in the HLA region possess distinct alleles which correlate strongly with specific HLA types. The length polymorphisms of the alleles are typically determined by PCR amplification using primers which flank the microsatellites.

"$(CA)_n$" refers to a repeated pattern of alternating cystine (C) and adenine (A) nucleotides in a DNA sequence, or GT (guanine and thymine nucleotides) on the complementary strand, wherein "n" refers to the number of repeating CA or GT units.

"DQCAR" refers to the polymorphic repetitive unit in the HLA DQ region between DQA1 and DQB1 and, more particularly, the HLA DQ region about 10 kb centromeric to the DQA1 gene and about 1–2 kb telomeric to the DQB1 gene. DQCAR can be amplified, for example, using the CAR1 and CAR2 primers of the present invention (SEQ ID NO. 1 and SEQ ID NO. 2 respectively).

"DQCARII" refers to the polymorphic repetitive unit in the HLA DQ region between DQA1 and DQB1, about 4–5 kb centromeric to the DQA1 gene. DQCARII can be amplified, for example, using the CADQFF and CADQR3 primers of the present invention (SEQ ID NO. 4 and SEQ ID NO. 5 respectively).

"G51152" refers to the repetitive unit located between DQB3 and DQB1, approximately 25–30 kb centromeric to DQB1. G51152 can be amplified, for example, using the G51152F and G51152R primers of the present invention (SEQ ID NO. 6 and SEQ ID NO. 7 respectively).

"HLA" is the abbreviation for human lymphocyte antigen, which is a system designation for the gene products of at least four linked loci (A, B, C, and D) on the sixth human chromosome.

"HLA associated diseases" refer to diseases associated with HLA. The term "associated with" generally means that the susceptibility of an organism to a subject disease is related to the presence of a particular sequence of DNA in the organisms genetic makeup, e.g., in the HLA region.

"Autoimmune diseases" refer to diseases arising from and directed against an individual's own tissues, for example, as identified by Sinha et al., "Autoimmune Disease: The Failure of Self Tolerance," Science 248: 1380–1388 (1990), which is incorporated herein by reference.

"Polymorphic" or "DNA polymorphism" refers to the condition in which two or more variations, or alleles, of a specific DNA sequence coexist in the same interbreeding population.

"Primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization in an appropriate buffer and at a suitable temperature. A primer is preferably an oligodeoxyribonucleotide and is single stranded for maximum efficiency in amplification, but may also be double stranded. If double stranded, the primer is first treated to separate its strands before being used to prepare extension products. A primer can be labeled, if desired, by incorporating a label detectable by spectroscopic, photochemical, biochemical, immunochemical or chemical means. Labels can also be used to capture the primer to facilitate the immobilization of either the primer or amplified DNA on a solid support.

"PCR" refers to the polymerase chain reaction, for example, as described in U.S. Pat. No. 4,683,202 (issued Jul. 28, 1987 to Mullis), which is incorporated herein by reference. PCR is an amplification technique wherein primers are hybridized to nucleic acid templates in the presence of a polymerization agent (such as polymerase) and four nucleotide triphosphates, and extension products are formed from the primers. These products are denatured and used as templates in a cycling reaction which amplifies the number and amount of existing nucleic acids to facilitate their subsequent detection. The amplification process can be carried out cyclically as many times as desired to produce a larger quantity of detectable material from a small amount of target nucleic acid sequence.

BRIEF DESCRIPTION OF THE DRAWINGS

FIG. 1 is a sequence (SEQ ID NO. 3) of the target region between DQA1 and DQB1 which includes DQCAR. The portions of the sequence corresponding to a preferred embodiment of CAR1 (SEQ ID NO. 1) and CAR2 (SEQ ID NO. 2) primers are indicated by the dashed underline and arrows. The portion of the sequence corresponding to the DQCAR microsatellite marker to be amplified is indicated by the solid underline.

DETAILED DESCRIPTION OF THE PREFERRED EMBODIMENTS

Figure 2:
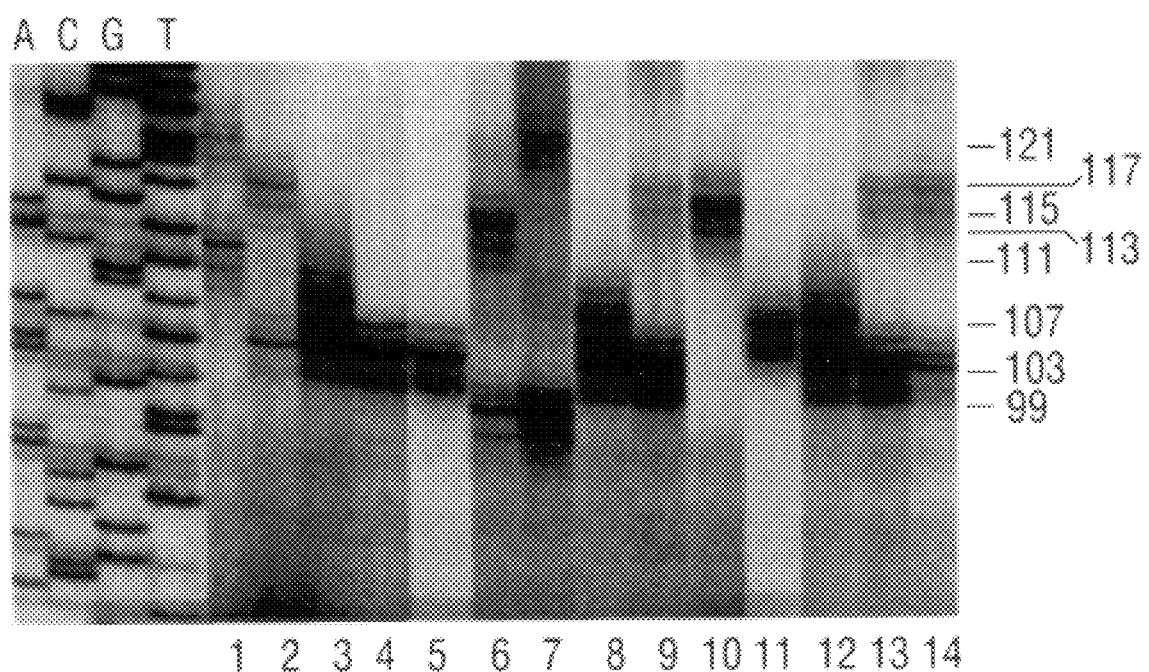
FIG. 2 is an x-ray film exposure of a sequencing gel indicating the DQCAR microsatellite polymorphism of samples from various subjects (lane 1 to 14). Amplification was performed with the CAR1 and CAR2 primers of SEQ ID NO. 1 and SEQ ID NO. 2 and the template in presence of 35S ATP and CTP. Amplified samples were then resolved on a 6% sequencing gel. ACGT indicates an M13mp18 sequence used as a size marker.

One embodiment of the present invention relates to the use of polymorphic microsatellite markers in the HLA region of the human genome for high resolution HLA typing. The specific markers disclosed herein are useful in HLA typing the DQ-DR region, based upon the finding that these markers give rise to distinct alleles which correlate strongly with specific HLA DQ/DR alleles. Based upon the association between alleles of the DQCAR, DQCARII, and G51152 microsatellites and specific DQ/DR alleles, this approach can be applicable to markers in other HLA regions. One of ordinary skill in the art would appreciate that the use of other microsatellite markers in the HLA region for high resolution HLA typing, assessing susceptibility to HLA associated disease, and evaluating the suitability of organ/tissue transplantation donors, is within the scope of the present disclosure.

A DNA sequence between the HLA DQA1 and DQB1 genes was provided by Satyanararayana and Strominger, Immunogenetics 35:235–240 (1992), which is incorporated herein by reference. The present inventors found that the sequence identified by Satyanararayana and Strominger contains a series of CA repeat units, $(CA)_n$, located approximately 10 kb centromeric to DQA1 and 1–2 kb telomeric to the DQB1 gene, referred to herein as "DQCAR."

DQCARII was isolated in our laboratory using an HLA class II cosmid cloning approach. Briefly, U16 or T16 cosmid DNA was digested with SauIIIA then ligated to a BamH1 cut, dephosphorylated pUC18 plasmid (Pharmacia). The resulting minilibrary was then transformed, plated, transferred and screened with the (CA)15 probe 5' end labeled with gamma-P32 ATP (T4 polynucleotide kinase, USB biochemical). DQCARII was isolated from U16 and is located between DQA1 and DQB1, 4 to 5 kb centromeric from DQA1. It can be PCR amplified, for example, using CADQFF (SEQ ID NO. 4) and CADQR3 (SEQ ID NO. 5) under cycling conditions of 95° C. for 30 sec, 58° C. for 1 min, and 72° C. for 1 min, for about 30 cycles. DQCARII was found to have at least 15 alleles (186, 188, 192, 194, 198, 200, 202, 204, 206, 208, 210, 212, 214, 216, 218 base pairs). Other primers could also be designed from the flanking region of the CA repeat.

G51152 is a CA repeat microsatellite located between DQB3 and DQB1, approximately 25–30 kb centromeric to DQB1. It was found to have at least 10 known alleles in tight linkage with HLA DQB1 (192, 194, 214, 216, 218, 220, 222, 226, 244 and 248 base pairs). G51152 primer information and PCR conditions were derived from available DNA sequence. It can be amplified, for example, using G51152F (SEQ ID NO. 6) and G51152R (SEQ ID NO. 7), under cycling conditions of 95° C. for 30 sec, 55° C. for 30 min, and 72° C. for 30 min, for about 35 cycles.

The following examples are provided to enable those of ordinary skill in the art to make and use the methods and compositions of the invention. These examples are not intended to limit the scope of what the inventors regard as their invention. Efforts have been made to ensure accuracy with respect to numbers used to characterize the measured conditions; however, some experimental errors and deviations may be present.

EXAMPLE I

Characterization of DQCAR in Human Ethnic Groups

A. Samples

Normal blood donors from Stanford University Blood Bank were randomly selected. Forty-one American-Caucasians, 40 African-Americans, 28 Mexican-Americans and 28 Asian-Americans (16 Chinese, 10 Japanese and 2 Korean) were HLA-DR and DQ typed by conventional lymphocyte microcytotoxicity. Two local families, one Caucasian and one Mexican-American, that had been serologically typed for HLA-DR and -DQ antigens were also available and were studied for Mendelian inheritance and establishment of haplotypes.

Cosmid clones from the homozygous B cell line Mann (DR7, DQ2), were provided by Dr. George Blanck, Harvard University, Cambridge, Mass. Blanck, et al., "Molecular Organization of the DQ Subregion (DO-DX-DV-SQ) of the Human MHC and its Evolutionary Implications", *J. Immunol.* 141:1734 (1988). The following cosmids were tested: T20, U11B, T16, M5, U16, U6C, U19A, U9B, spanning from DOB to DQA1 region.

Well characterized B-cell lines from the Tenth Histocompatibility Workshop and selected samples from a panel of oligotyped Japanese subjects were mostly used. All samples had been previously oligotyped for HLA class II DRB1, DQA1, DQB1 genes using conventional methods. Yang et al., "Description of the Reference Panel of B-lymphoblastoid Cell Lines For Factors of the HLA System: The B-cell Line Panel Designed for the Tenth International Histocompatibility Workshop," *Immunobiology of HLA* (Vol. 1) Histocompatibility Testing (1987); Kimura et al., "DNA Typing of HLA Class II Genes in B-lymphoblastoid Cell Lines Homozygous for HLA," *Tissue Antigens* 40:5 (1992); Fernandez-Vina et al., "Alleles at Four HLA Class II Loci Determined by Oligonucleotide Hybridization and Their Association in Five Ethnic Groups," *Immunogenetics* 34:299 (1991); Gyllensten et al., "MHC Class II Haplotypes and Linkage Disequilibrium in Primates," *Human Immunology* 36:1 (1993); and Aldener et al., "Characterization of a Novel DQB1 (DQB1*0609) Allele by PCR Amplification with Sequence-specific Primers (PCR-SSP) and Nucleotide Sequencing," *Tissue Antigens* 42:536 (1993).

Full DQA1 and DQB1 sequencing and/or oligotyping was also performed on individual workshop cell lines, this leading to the identification of a few new DQA1 and DQB1 allelic combinations: DQA1*01021 and DQA1*01022 (codon 109, ATT vs ATC respectively, Gene Bank Accession numbers L34083 and L34084 in cell lines 9097 and 9009 respectively) associated with DQB1*06 and DQB1*0502; DQA1*0104 (codon 2 GGC vs GAC, codon 199 ACC vs GCC for DQA1*0104 vs DQA1*0101, Gene Bank Accession number L34086 for cell line 9054) associated with the DRB1*14,DQB1*05 haplotypes, previously oligotyped as DQA1*0101; DQA1*0502 (codon 160, TCT vs GCT for DQA1*05011, Gene Bank Accession number L34093 for cell line 9064) associated with the DRB1*14, DQB1*0301 haplotype previously oligotyped as DQA1*0501 by exon 2 analysis; and DQB1*0202 (codon 135, GGT vs GAT for DQB1*0201, Gene Bank Accession L34095 for cell line 9050) associated with the DRB1*07, DQA1*0201 haplotype previously thought as DQB1*0201. The presence of these new subtypes was also analyzed by oligotyping in the panel studied together with DQA1*0301 and DQA1*0302. Fernandez-Vina et al., "DQA1*03 Subtypes Have Different Associations with DRB1 and DQB1 Alleles," *Human Immunology* 39:290–298 (1994).

Finally, DNA from the following cells or cell lines, selected because of unusual HLA types, were also used: sample of DRB1*0104 (Guignier et al., "A novel HLA-DRB1*01 allele (DRB1*0104)," *Tissue Antigens* 42:42 (1993)); samples of DRB1*1407 and DRB1*1408 (Dong et al., "Sequence Analysis of Three Novel DRw14-DRB1 Alleles," *Immunogenetics* 36:130–133 (1992)); cells Ter 120, 126, 130 (Terasaki Exchange cell panel, UCLA, Los Angeles Calif.), typed serologically and by PCR allele specific amplification (Olerup et al., "HLA-DR Typing by PCR Amplification with Sequence-specific Primers (PCR-SSP) in 2 hours: An Alternative to Serological DR typing in Clinical Practice Including Donor-recipient Matching in Cadaveric Transplantation," *Tissue Antigens* 39:225 (1992) and Olerup et al., "HLA-DQB1 and DQA1 Typing by PCR Amplification with Sequence-specific Primers (PCR-SSP) in 2 Hours," *Tissue Antigens* 41: 199 (1993)); cell 2708 (DQA1*0104-DQB1*0605) (Lee et al., "Two Divergent Routes of Evolution Gave Rise to the DRw13 Haplotypes," *J. Immunol* 145:3119 (1990) and Lee et al., "New DQw1 Diversity Identified Within DRw12 and DRw14 Haplotypes," *Tissue Antigens* 38:231 (1991)); cell lines number 73, 79 and 106, from UCLA DNA reference panel, UCLA, Los Angeles, Calif., were oligotyped by laboratories participating in the International Cell Exchange Program; sample from a person with a rare DR3,DQ1 haplotype (Caucasian narcoleptic patient from Norway (Ronningen et al., "Novel HLA-DR2 and DR3 Haplotypes Among Norwegian Caucasians," *Tissue Antigens* 37:165 (1991)) confirmed by family study (Mignot et al., "A Novel HLA DR17,DQ1 (DQA1-0102/DQB1-0602 Positive) Haplotype Predisposing to Narcolepsy in Caucasians," *Sleep* 16:764 (1993)) and samples of DQB1*0607 and DQB1*0608 cells (Fenske et al., "Two Novel HLA-DQB1*06 Alleles Reveal Additional Heterogeneity of HLA-DQw1," *Tissue Antigens* 40:49 (1992)).

B. Design of Primers

The sequence of the microsatellite region obtained from Satyanarayana and Strominger, *Immunogenetics* 35:235–240 (1992), is from cosmids U6C and U16 from cell line Mann (DR7, DQ2). A $(CA)_{22}$ repeating element is located approximately 10 kb centromeric to DQA1 and 1–2 kb telomeric to the DQB1 gene beginning at base pair 33. The software PRIMER (Version 0.5, Whitehead Institute, Cambridge, Mass.) was used to design primers surrounding the $(CA)_n$ repeat segment. Different sets of oligonucleotides (CAR1, CAR2) were tested, and the best combination (SEQ ID NO. 1: 5' GAAACATATATTAACAGAGACAGACAAA 3', and SEQ ID NO. 2: 5' CATTTCTCTTCCTTATCACT-TCATA 3') was selected for further studies. The location of the primers in the microsatellite sequence is shown in FIG. 1.

C. DQCAR Amplification

Genomic DNA (200 ng) was used as a template, in a total volume of 25 μl of 10 mM Tris-HCl, pH 8.3, 50 mM KCl, 1.5 mM $MgCl_2$, 50 pmol of each primer (CAR1 (SEQ ID NO. 1) and CAR2 (SEQ ID NO. 2)), 125 μM of dGTP and dTTP, 4 μM of dATP and dCTP, 2 μCi of α($^{35}$S)dATP and α($^{35}$S)dCTP (both from Amersham Corporation, Arlington Heights Ill.) and 1 U AmpliTaq DNA polymerase (Applied Biosystems, South San Francisco, Calif.). The amplification was performed with 30 cycles (94° C., 30 sec, 57° C., 1 min; and 72° C. 1 min).

D. Determination of DQCAR Alleles

Samples were analyzed by electrophoresis on a 6% denaturing polyacrylamide gel. The size of the amplified fragment was determined using an M13 mp18 sequencing ladder (US Biochemicals, Cleveland, Ohio). In some cases where an unexpected result was obtained (e.g., observation of a rare allele, or of different DQCAR alleles in cell lines with the same oligotyping profile), HLA-DR and -DQ were rechecked using allele specific PCR amplification.

The size of the allele was also verified several times by running other samples with similar sizes side by side with the sample of interest. After running the samples, the gel was dried without fixation and exposed to X-ray film as shown in FIG. 2.

E. Calculation of Allele and Haplotype Frequencies

Microsatellite allele frequencies were calculated as described by Falconer, *Introduction to Quantitative Genetics*, New York Longman Scientific and Technical (1989). Haplotypic frequencies, linkage disequilibrium (delta value), relative delta value and chi-square were calculated as described in Imanishi et al., "HLA 1991 Proceedings of the Eleventh International Histocompatibility Workshop and Conference," New York (1992).

F. Amplification of DQCAR in Cosmids Spanning the HLA DQ Region

Initially, cosmids from the cell line Mann were tested, in order to verify the amplification of the DQCAR within the class II region. Eight cosmid clones spanning from the DOB to the DQA1 locus were used. Using the primers CAR1 (SEQ ID NO. 1) and CAR2 (SEQ ID NO. 2), only cosmids U16 and U6C amplified, thus confirming the location of DQCAR 1–2 kb telomeric to the DQB1 gene. The size of the allele amplified was 121 base pairs (bp, DQCAR 121), as predicted by the sequence of Satyanarayana and Strominger.

G. DQCAR Alleles Observed in the Selected Panel of HLA Well Characterized Cells and Cell Lines Seventy-five B cell lines from the Tenth Histocompatibility Workshop and twenty-eight Japanese cells oligotyped for HLA-DRB1, DQA1 and DQB1 alleles were tested, along with sixteen other HLA class II characterized cells and cell lines (Table 1). In this panel, ten DQCAR alleles were observed and identified by differences in length of the amplified fragments. As reported for most $(CA)_n$ microsatellites, the size of the PCR products observed varied by 2 bp between alleles. The DQCAR sizes observed were 99, 103, 107, 109, 111, 113, 115, 117, 119 and 121 base pairs (total size of the PCR product). Two possible allele sizes, DQCAR 101 and 105, were not detected.

The most striking finding was the observation that almost all DQ1 (DQ5 and DQ6) associated haplotypes shared the same DQCAR allele, DQCAR 103, and more rarely DQCAR 107, independent of any DRB1 polymorphism. For all other haplotypes, i.e., DQ2, DQ3 (DQ7, DQ9) and DQ4, greater DQCAR polymorphism was seen, with DQCAR 103 always being absent.

The DQ7 subtype showed the greatest polymorphism of all DQ types, with seven different DQCAR alleles observed (DQCAR 111 to 121). A particularly interesting observation was that different DQCAR alleles were observed within the same DQA1/DQB1 haplotypic combinations. DQA1*0501/DQB1*0301 haplotypes, for example, showed 4 different alleles, DQCAR 115, 117, 119, and 121.

In some cases, different DQCAR alleles were observed even though the extended haplotype was the same at the DRB1-DQA1-DQB1 loci, e.g., cell lines 9039 and 9040 (DRB1*1102, DQA1*05013, DQB1*0301). This was also observed with DR7, DQ2 haplotypes and for some DQ4 extended haplotypes (see Table 1).

TABLE 1

HLA Haplotypes and Their Corresponding DQCAR Alleles in the Cell Line Panel

| Sample | DR | DRB1 | DQ | DQA1 | DQB1 | DQCAR (bp) | Ethnic group |
|---|---|---|---|---|---|---|---|
| 9003–06, 9080 | 1 | 0101 | 5 | 0101 | 0501 | 103 | C |
| K63095[a] | 1 | 0101 | 5 | 0101 | 0501 | 103 | O |
| 9002, 90178 | 1 | 0102 | 5 | 0101 | 0501 | 103 | C |
| K62114[a] | 10 | 1001 | 5 | 0104 | 0501 | 103 | O |
| DRB1* 0104[a,b] | nt | 0104 | nt | 01 | 05 | 103 | C |
| 9007[a] | 16 | 1602 | 5 | 01022 | 0502 | 103 | C |
| 9036 | 11 | 1101 | 5 | 01022 | 0502 | 103 | C |
| 9009, 9012 | 16 | 1601 | 6 | 01022 | 0502 | 103 | C |
| Ter130[a,c] | 15 | nt | 5 | nt | 0502 | 103 | O |
| K90094[a], K60083[a] | 14 | 1401 | 5 | 0104 | 0502 | 103 | O |
| 9054, 9056[a], 9057, 9061 | 14 | 1401 | 5 | 0104 | 05031 | 107 | C |
| K62049[a] | 14 | 1401 | 5 | 0104 | 05031 | 107 | O |
| K90010[a], K90031[a] | 14 | 1405 | 5 | 0104 | 05031 | 107 | O |
| K90066[a], K62049[a], K61118[a] | 14 | 1405 | 5 | 0104 | 05031 | 109 | O |
| PNG196[a,e] | 14 | 1407 | 5 | 0104 | 05031 | 107 | NG |
| PNG198[e], PNG202[a,e] | 14 | 1408 | 5 | 0104 | 05031 | 107 | NG |
| 9011 | 15 | 1502 | 6 | 0103 | 0601 | 107 | C |
| K90025[a], K90036[a], K90061[a], K62042[a] | 15 | 1502 | 6 | 0103 | 0601 | 107 | O |
| 9066, Ter126[a,c], K90008[a], K62097[a] | 8 | 08032 | 6 | 0103 | 0601 | 107 | O |
| Ter120[a,c] | 14 | 1401 | 6 | nt | 0602 | 103 | B |
| #73[a,f] | nt | 1501 | nt | 0102 | 0602 | 103 | C |
| 9008[a], 9013–14, 9017, 9081–83 | 15 | 1501 | 6 | 01021 | 0602 | 103 | C |
| K90002[a], K62114[a], K90083[a], K80049[a] | 15 | 1501 | 6 | 01021 | 0602 | 103 | O |
| PNG196[a] | 15 | 1501 | 6 | 01021 | 0602 | 103 | NG |
| 9010 | 15 | 1503 | 6 | 01021 | 0602 | 103 | C |
| ANH[a,g] | 17 | 0301 | 6 | 0102 | 0602 | 103 | C |
| 9008[a] | 15 | 1501 | 6 | 01021 | 0603 | 103 | C |
| 9060, 9062, 9065 | 13 | 1301 | 6 | 0103 | 0603 | 103 | C |
| 9058 | 13 | 1301 | 6 | 0103 | 0603 | 103 | B |
| 9056[a], 9063, 9097 | 13 | 1302 | 6 | 01021 | 0604 | 103 | C |
| K90005[a], K90031[a], K90068[a], K90072[a] | 13 | 1302 | 6 | 01021 | 0604 | 103 | O |
| K90008[a], K80049[a] | 13 | 1302 | 6 | 01021 | 0605 | 103 | O |
| 2708[a,d] | 12 | 1201 | 5 | 0104 | 0605 | 103 | B |

TABLE 1-continued

HLA Haplotypes and Their Corresponding DQCAR Alleles in the Cell Line Panel

| Sample | DR | DRB1 | DQ | DQA1 | DQB1 | DQCAR (bp) | Ethnic group |
|---|---|---|---|---|---|---|---|
| DQB1*0607[a,h] | nt | 06 | nt | 0103 | 0607 | 103 | B |
| DQB1*0608[a,h] | nt | 1302 | nt | 0102 | 0608 | 103 | B |
| 9055[i] | 6 | 1302 | 6 | 01021 | 0609 | 103 | C |
| 2708[a,d] | 13 | 1303 | 2 | 0201 | 02 | 113 | B |
| DQB1*0607[a,h] | nt | 07 | nt | 0201 | 02 | 115 | B |
| 9047, 9048, 9093 | 7 | 0701 | 2 | 0201 | 0202 | 113 | C |
| 9051 | 7 | 0701 | 2 | 0201 | 0202 | 121 | C |
| Ter120[a,c] | 17 | 0301 | 2 | nt | 02 | 99 | B |
| DRB1*0104[a,b] | nt | 03 | nt | 05 | 02 | 99 | C |
| 9086–88 | 3 | 0301 | 2 | 05011 | 0201 | 99 | C |
| 9018–20, 9022–23 | 17 | 0301 | 2 | 05011 | 0201 | 99 | C |
| 9025, 9091 | 4 | 0401 | 7 | 0302 | 0301 | 117 | C |
| 9030 | 4 | 0407 | 7 | 0302 | 0301 | 119 | C |
| 9016 | 16 | 1602 | 7 | 05013 | 0301 | 115 | AI |
| 9035 | 11 | 1101 | 7 | 0501 | 0301 | 121 | C |
| ANH[a,g] | 11 | nt | 7 | 05013 | 0301 | 121 | C |
| 9043 | 11 | 1101 | 7 | 05013 | 0301 | 121 | C |
| 9039 | 11 | 1102 | 7 | 05013 | 0301 | 121 | C |
| 9040 | 11 | 1102 | 7 | 05013 | 0301 | 117 | C |
| 9042 | 11 | 1103 | 7 | 05013 | 0301 | 121 | C |
| K62097[a] | 14 | 1402 | 7 | 05013 | 0301 | 117 | O |
| 9045[a], 9089 | 11 | 1104 | 7 | 05013 | 0301 | 121 | C |
| 9045[a] | 12 | 1201 | 7 | 05013 | 0301 | 117 | C |
| K90039[a], K90084[a] | 12 | 1201 | 7 | 05013 | 0301 | 117 | O |
| DQB1*0608[a,h], #79[a,f] | nt | 1303 | nt | 0501 | 0301 | 119 | B |
| K900068[a], K90080[a], K90094[a] | 14 | 1406 | 7 | 0502 | 0301 | 117 | O |
| 9064, 9099 | 14 | 1402 | 7 | 0502 | 0301 | 117 | AI |
| K90002[a], K90005[a] | 14 | 1403 | 7 | 0502 | 0301 | 117 | O |
| #73[a,f] | nt | 0103 | nt | 05 | 0301 | 121 | C |
| K62033[a] | 8 | 0802 | 7 | 0601 | 0302 | 111 | O |
| 9070 | 8 | 08032 | 7 | 0601 | 0301 | 113 | C |
| K90061[a], K90072[a] | 12 | 1202 | 7 | 0601 | 0301 | 113 | O |
| 9007[a], 9029, 9031–32 | 4 | 0401 | 8 | 0301 | 0302 | 111 | C |
| 9026 | 4 | 0402 | 8 | 0301 | 0302 | 111 | C |
| K90084[a] | 4 | 0403 | 8 | 0301 | 0302 | 113 | O |
| 9092 | 4 | 0404 | 8 | 0301 | 0302 | 111 | C |
| 9028 | 4 | 0404 | 8 | 0301 | 0302 | 111 | AI |
| K90111[a] | 4 | 0407 | 8 | 0301 | 0302 | 111 | O |
| K-UT2, K90036[a] | 4 | 0406 | 8 | 0301 | 0302 | 111 | O |
| K62088[a] | 8 | 0802 | 8 | 0301 | 0302 | 113 | O |
| 9034 | 4 | 0401 | 8 | 0302 | 0302 | 111 | C |
| 9052 | 7 | 0701 | 9 | 0201 | 03032 | 119 | C |
| Ter130[a,c] | 9 | nt | 3 | nt | nt | 115 | O |
| 9076 | 9 | 0901 | 3 | 0302 | 03032 | 115 | C |
| K90010[a], K90111[a] | 9 | 0901 | 3 | 0302 | 03032 | 115 | O |
| Ter126[a,c] | 9 | 0901 | 9 | 03 | 0303 | 115 | O |
| 9075 | 9 | 0901 | 9 | 0302 | 03032 | 117 | C |
| PNG202[a,e] | 9 | 0901 | 9 | 0302 | 03032 | 117 | NG |
| #106[f] | nt | 0405 | nt | 03 | 0401 | 113 | O |
| K90066[a], K90080[a], K61118[a], | 4 | 0405 | 4 | 0302 | 0401 | 113 | O |
| K62088[a] 9107, K63095[a] K60083[a] | 4 | 0405 | 4 | 0302 | 0401 | 115 | O |
| K90039[a], K90083[a] | 4 | 0410 | 4 | 0302 | 0402 | 113 | O |
| #79[a,f] | nt | 0302 | nt | 0401 | 0402 | 119 | B |
| 9021 | 18 | 0302 | 4 | 0401 | 0402 | 117 | B |
| 9067–9069 | 8 | 0801 | 4 | 0401 | 0402 | 113 | C |
| 9071, 9072 | 8 | 0802 | 4 | 0401 | 0402 | 117 | AI |
| K90025[a] | 8 | 0802 | 4 | 0401 | 0402 | 117 | O |

All cell lines with numbers starting with 90 are from the Tenth International HLA Workshop. Cells starting with K are selected Japanese control subjects oligotyped by the inventors. DR and DQ oligotyping is reported as described in the literature and confirmed by the inventors, with the exceptions of a few newly described haplotypic combinations. nt, not tested. C, Caucasian, B, Black, O, Oriental, AI, American Indians, NG, New Guinea Melanesians. [a] Heterozygous cells: the DR, DQ, DQCAR alleles present have been assigned to the most likely haplotype combinations; [b] Guignier et al., "A Novel HLA-DRB1*01 Allele (DRB1*0104)," Tissue Antigens 42:42 (1992); [c] International Cell Exchange (Dr. Paul I. Terasaki, UCLA, Los Angeles Calif.); [d] Lee et al., "Two Divergent Routes of Evolution Gave Rise to the DRw13 Haplotypes," J. Immunol. 145:3119 (1990) and Lee et al., "New DQw1 Diversity Identified Within DRw12 and DRw14 Haplotypes," Tissue Antigens 38:231 (1991); [e] Dong et al., "Sequence Analysis of Three Novel DRw14-DRB1 Alleles," Immunogenetics 36:130–133 (1992); [f] UCLA DNA Reference Panel; [g] Mignot et al., "A Novel HLA DR17,DQ1 (DQA1-0102/DQB1-0602 Positive) Haplotype Predisposing to Narcolepsy in Caucasians," Sleep 16:764 (1993); [h] Fenske et al., "Two Novel HLA-DQB1*06 Alleles Reveal Additional Heterogeneity of HLA-DQw1," Tissue Antigens 40:49 (1992); [i] Aldener et al., "Characterization of a Novel DQB1 (DQB1*0609) Allele by PCR Amplification with Sequence-Specific Primers (PCR-SSP) and Nucleotide Sequencing," Tissue Antigens 42:536 (1993).

TABLE 2

HLA-DR and -DQ Alleles Frequencies in Four Local Ethnic Groups

| HLA | American-Caucasian N = 80 | African-American N = 70 | Mexican-American N = 56 | Asian-American N = 54 |
|---|---|---|---|---|
| HLA-DR | | | | |
| DR1 | 0.112 | 0.086 | 0.053 | nf |
| DR2 | 0.125 | 0.129 | 0.161 | 0.259 |
| DR3 | 0.125 | 0.129 | 0.053 | 0.093 |
| DR4 | 0.125 | 0.086 | 0.214 | 0.222 |
| DR5 | 0.100 | 0.142 | 0.142 | 0.074 |
| DR6 | 0.162 | 0.200 | 0.161 | 0.093 |
| DR7 | 0.187 | 0.129 | 0.125 | 0.037 |
| DR8 | 0.025 | 0.071 | 0.089 | 0.129 |
| DR9 | 0.012 | nf | nf | 0.093 |
| DR10 | 0.025 | 0.028 | nf | nf |
| HLA-DQ | | | | |
| DQ1 | 0.437 | 0.500 | 0.286 | 0.463 |
| DQ2 | 0.287 | 0.229 | 0.179 | 0.129 |
| DQ3 | 0.250 | 0.214 | 0.517 | 0.241 |
| DQ4 | 0.025 | 0.057 | 0.017 | 0.148 |

Data shown are gene frequencies.
N refers to total number of haplotypes studied in each ethnic group; nf, not found in the sample studied.

TABLE 3

DQCAR Alleles Frequencies in Four Local Ethnic Groups

| DQCAR allele | American-Caucasian N = 80 | African-American N = 70 | Mexican-American N = 56 | Asian-American N = 54 |
|---|---|---|---|---|
| 99  | 0.125 | 0.129 | 0.054 | 0.093 |
| 103 | 0.388 | 0.471 | 0.214 | 0.222 |
| 105 | 0.012 | 0.014 | nf    | nf    |
| 107 | 0.038 | 0.014 | 0.071 | 0.241 |
| 111 | 0.112 | 0.057 | 0.232 | 0.093 |
| 113 | 0.088 | 0.086 | 0.018 | 0.166 |
| 115 | 0.012 | 0.014 | 0.054 | 0.093 |
| 117 | 0.050 | 0.172 | 0.089 | 0.055 |
| 119 | 0.025 | 0.029 | 0.054 | nf    |
| 121 | 0.138 | 0.014 | 0.196 | 0.037 |
| 123 | 0.012 | nf    | 0.018 | nf    |

Data shown are gene frequencies.
N refers to total number of chromosomes studied in each ethnic group;
nf, not found in the sample studied.

TABLE 4

HLA-DQ/DQCAR Haplotype Frequencies, Linkage Disequilibrium (delta value), Relative Delta Value and Chi-square Values in Four Local Ethnic Groups

| HLA-DQ | DQCAR | HF | LD | RLD | $X^2$ |
|---|---|---|---|---|---|
| American Caucasian N = 80 | | | | | |
| DQ1 | 103 | 0.389 | 0.219 | 1.00 | 66.11*** |
| DQ1 | 107 | 0.037 | 0.021 | 1.00 | 4.01* |
| DQ2 | 99  | 0.125 | 0.089 | 1.00 | 28.31*** |
| DQ2 | 113 | 0.062 | 0.037 | 0.60 | 6.80** |
| DQ2 | 121 | 0.062 | 0.023 | 0.23 | 1.7$^{ns}$ |
| DQ3 | 111 | 0.087 | 0.059 | 0.70 | 15.07*** |
| DQ3 | 117 | 0.038 | 0.025 | 0.66 | 5.6* |
| DQ3 | 119 | 0.025 | 0.019 | 1.00 | 6.15* |
| DQ3 | 121 | 0.075 | 0.040 | 0.40 | 5.93* |
| DQ4 | 113 | 0.025 | 0.023 | 1.00 | 21.36*** |
| African-American N = 70 | | | | | |
| DQ1 | 103 | 0.471 | 0.236 | 1.00 | 62.42*** |
| DQ2 | 99  | 0.129 | 0.099 | 1.00 | 34.82*** |
| DQ2 | 113 | 0.071 | 0.052 | 0.79 | 13.59*** |
| DQ3 | 111 | 0.057 | 0.045 | 1.00 | 15.5*** |
| DQ3 | 117 | 0.100 | 0.063 | 0.47 | 11.73*** |
| DQ3 | 119 | 0.022 | 0.022 | 1.00 | 6.91** |
| DQ4 | 117 | 0.042 | 0.032 | 0.68 | 9.40** |
| Mexican-American N = 56 | | | | | |
| DQ1 | 103 | 0.214 | 0.153 | 1.00 | 35.11*** |
| DQ1 | 107 | 0.071 | 0.051 | 1.00 | 10.77** |
| DQ2 | 99  | 0.054 | 0.044 | 1.00 | 14.57*** |
| DQ2 | 119 | 0.036 | 0.026 | 0.59 | 5.13* |
| DQ2 | 121 | 0.071 | 0.036 | 0.25 | 3.19$^{ns}$ |
| DQ3 | 111 | 0.232 | 0.112 | 1.00 | 15.79*** |
| DQ3 | 115 | 0.054 | 0.026 | 1.00 | 2.97$^{ns}$ |
| DQ3 | 117 | 0.071 | 0.025 | 0.58 | 1.73$^{ns}$ |
| DQ3 | 121 | 0.125 | 0.090 | 0.56 | 19.59*** |
| Asian-American N = 54 | | | | | |
| DQ1 | 103 | 0.222 | 0.119 | 1.00 | 17.81*** |
| DQ1 | 107 | 0.241 | 0.129 | 1.00 | 19.76*** |
| DQ2 | 99  | 0.093 | 0.081 | 1.00 | 37.38*** |
| DQ2 | 113 | 0.037 | 0.016 | 0.15 | 0.89$^{ns}$ |
| DQ3 | 111 | 0.074 | 0.051 | 0.72 | 9.10** |
| DQ3 | 115 | 0.074 | 0.051 | 0.72 | 9.10** |
| DQ3 | 117 | 0.037 | 0.024 | 0.57 | 3.27** |
| DQ3 | 121 | 0.037 | 0.028 | 1.00 | 6.50* |
| DQ4 | 113 | 0.111 | 0.086 | 0.70 | 22.88*** |

Values were estimated only when the corresponding haplotypes were observed more than once in the specific ethnic group. Rare haplotype are thus not included.
N refers to total number of haplotypes studied in each ethnic group.
HF, Haplotype Frequency.
LD, Linkage Disequilibrium, (delta value);
RLD, Relative Delta Value,
$c^2$, Chi-Square. For details, see Song et al., "Recombination Between DQa and DQb Genes Generates Human Histocompatibility Leukocyte Antigen Class II Haplotype Diversity," J. Immunol 139:2993 (1987)
$^{ns}$not statistically significant
*p < 0.05.
**p <0.01.
***p < 0.001.

TABLE 5

Number and Frequency of Individual HLA-DR, DQ, DQCAR Extended Haplotypes in Four Local Ethnic Groups

| DR | DQ | DQCAR | American-Caucasian N = 80 n(HF) | African-American N = 70 n(HF) | Mexican-American N = 56 n(HF) | Asian-American N = 54 n(HF) |
|---|---|---|---|---|---|---|
| a) haplotypes identified in the cell line panel (see table 1) | | | | | | |
| DR1 | DQ1 | 103 | 8(0.100) | 5(0.071) | 3(0.054) | nf |
| DR2 | DQ1 | 103 | 9(0.112) | 9(0.129) | 5(0.089) | 9(0.166) |
|     |     | 107 | 1(0.012) | nf | 1(0.018) | 4(0.074) |
| DR2 | DQ3 | 115 | nf | nf | 3(0.054) | nf |
| DR3 | DQ2 | 99  | 10(0.125) | 9(0.129) | 3(0.054) | 5(0.093) |
| DR4 | DQ3 | 111 | 7(0.087) | 4(0.057) | 12(0.214) | 4(0.074) |
|     |     | 117 | 3(0.038) | 2(0.028) | nf | 1(0.018) |
| DR4 | DQ4 | 113 | nf | nf | nf | 7(0.130) |
|     |     | 115 | nf | nf | nf | 1(0.018) |
| DR5 | DQ1 | 103 | 1(0.012) | 6(0.086) | nf | nf |
| DR5 | DQ3 | 117 | nf | 4(0.057) | 1(0.018) | 1(0.018) |
|     |     | 121 | 6(0.075) | nf | 5(0.089) | 2(0.037) |
| DR6 | DQ1 | 103 | 11(0.138) | 11(0.157) | 4(0.071) | 2(0.037) |
|     |     | 107 | 2(0.025) | 1(0.014) | 3(0.054) | 3(0.056) |
| DR6 | DQ3 | 117 | nf | 1(0.014) | 1(0.018) | nf |
| DR7 | DQ2 | 113 | 5(0.062) | 5(0.071) | 1(0.018) | 2(0.037) |
|     |     | 115 | nf | 1(0.014) | nf | nf |
|     |     | 121 | 5(0.062) | nf | 4(0.071) | nf |
| DR7 | DQ3 | 119 | 2(0.025) | 2(0.029) | nf | nf |
| DR8 | DQ1 | 107 | nf | nf | nf | 4(0.074) |
| DR8 | DQ3 | 111 | nf | nf | 1(0.018) | nf |
|     |     | 113 | nf | nf | nf | 1(0.018) |
| DR8 | DQ4 | 113 | 2(0.025) | 1(0.014) | nf | nf |
|     |     | 117 | nf | 3(0.042) | 1(0.018) | 1(0.018) |
| DR9 | DQ3 | 115 | 1(0.012) | nf | nf | 4(0.074) |
| DR10| DQ1 | 193 | 2(0.025) | 2(0.028) | nf | nf |
| b) Additional haplotypes not identified in the cell line panel | | | | | | |
| DR1 | DQ1 | 105 | 1(0.012) | 1(0.014) | nf | nf |
| DR5 | DQ1 | 107 | nf | nf | nf | 1(0.018) |
| DR5 | DQ3 | 119 | nf | nf | 1$^a$(0.018) | nf |
|     |     | 123 | 1(0.012) | nf | 1(0.018) | nf |
| DR6 | DQ3 | 121 | nf | 1(0.014) | 1(0.018) | nf |
| DR7 | DQ2 | 111 | 2(0.025) | nf | nf | nf |
|     |     | 113 | 1$^a$(0.012) | 1(0.014) | nf | nf |
|     |     | 119 | nf | nf | 2(0.036) | nf |

TABLE 5-continued

Number and Frequency of Individual HLA-DR, DQ, DQCAR Extended Haplotypes in Four Local Ethnic Groups

| Haplotype | | | American-Caucasian N = 80 | African-American N = 70 | Mexican-American N = 56 | Asian-American N = 54 |
|---|---|---|---|---|---|---|
| DR | DQ | DQCAR | n(HF) | n(HF) | n(HF) | n(HF) |
| DR8 | DQ1 | 103 | nf | nf | nf | 1(0.018) |
| DR8 | DQ3 | 117 | nf | 1(0.014) | 2(0.036) | nf |
|  |  | 121 | nf | nf | 1(0.018) | nf |

N refers to total number of haplotypes studied in each ethnic group.
n, number of haplotypes detected in each group.
HF, corresponding haplotype frequency.
nf, not found in our panel of control subjects.
<sup>a</sup>segregation of this haplotype was observed in one case.

H. HLA Typing Results in Samples of Randomly Selected Controls.

The allele frequencies for HLA-DR and -DQ in the 4 different groups studied are listed in Table 2. The frequency of the various antigens was found to be similar to previously reported results for Caucasians, African-Americans and Mexicans (Imanishi et al., "Allele and Haplotype Frequencies for HLA and Complement Loci in Various Ethnic Groups," HLA 1991—Proceedings of the Eleventh International Histocompatibility Workshop and Conference, New York (1992)). For Asian-Americans, the sample is a heterogeneous collection of subjects of Chinese, Japanese and Korean descent (16, 10 and 2 subjects respectively) that are representative of the San Francisco geographical area.

I. DQCAR Allele Frequencies Among Four Ethnic Groups

Of the 137 randomly selected samples initially included in the study, all amplified, except for one Caucasian and 5 African American DNA samples using CAR1 and CAR2 (96%). These six samples were excluded from the study. The six excluded samples either did not amplify on two successive attempts using two DNA preparations (1 sample) or were unavailable for another DNA extraction. These samples did not share a specific HLA type. A few additional samples that failed initially to amplify were successfully amplified after a new DNA extraction and were included in the study.

Four ethnic groups were tested (Caucasian-, African-, Mexican- and Asian-American) and the same DQCAR alleles were found in all ethnic groups. Allele frequencies in each ethnic group are reported in Table 3. The most common alleles found were DQCAR 103 in Caucasian- and African-Americans, DQCAR 111 in Mexican-Americans and DQCAR 107 in Asian-Americans. Two rare new DQCAR alleles, DQCAR 105 and 123, not observed in our extensive cell line panel survey, were detected. DQCAR 109, an allele found in association with DRB1*1405, DQA1*0104, DQB1*05031 in our panel of oligotyped Japanese subjects was not found in our population survey. A total of 12 DQCAR alleles (defined by length polymorphism) were therefore observed.

J. Linkage Disequilibrium of DQCAR for DQ in Randomly Selected Subjects

Linkage disequilibrium (delta value), relative delta value and chi-square for each DQCAR association in each population were calculated (Table 4). Only haplotypes observed more than once were used for the calculations.

Significant linkage disequilibrium was found between most DQ types and specific DQCAR alleles (Table 4). Linkage disequilibrium was especially high between DQ1 and DQCAR 103 in each ethnic group, consistent with the observation in our cell line panel. Another association of interest was observed between DQ2 and DQCAR 99 in each ethnic group. This association probably arises from the occurrence of only one DQ2 haplotype of high frequency, DR3, DQ2, whereas the DQ1, DQCAR 103 association included a large number of very diverse DQ1 associated haplotypes.

K. Analysis of Haplotypes Extended to Include HLA-DR

HLA-DR, DQ, DQCAR haplotypes were deduced in our population using known DR, DQ associations from the Tenth Workshop, from our panel of B cell lines and other cells characterized in Table 1 and in family studies. To do so, we assumed that the DQ and the DQCAR have no blanks and gave priority to combinations already observed with the characterized cells. New or very rare haplotypes were considered only when the opposing haplotype was well defined and highly likely, or when family studies could be performed (2 cases). Using these assumptions, it was possible to deduce HLA-DR, DQ, DQCAR haplotypes in all cases but one (a Chinese subject). This individual was therefore excluded from the study.

Twenty six haplotypes observed in the population studies corresponded to haplotypes previously identified using our cell line panel (Table 5, part a). Eleven new haplotypes were also observed, mostly in less well studied ethnic groups such as the Mexican Americans (6 haplotypes). These, mostly rare haplotypes, are listed in Table 5, part b.

In general, these new haplotypic combinations of the population studies confirmed and extended observations in cell lines. All new DQ1 associated haplotypes included either DQCAR 103 or 107, with the exception of the very rare DQCAR 105. Of the 11 new haplotypes, 5 were DQ3 bearing haplotypes with a DQCAR allele ranging from 117–123 bp, showing that the greatest haplotypic diversity is found within this DQ subtype.

Figure 3:
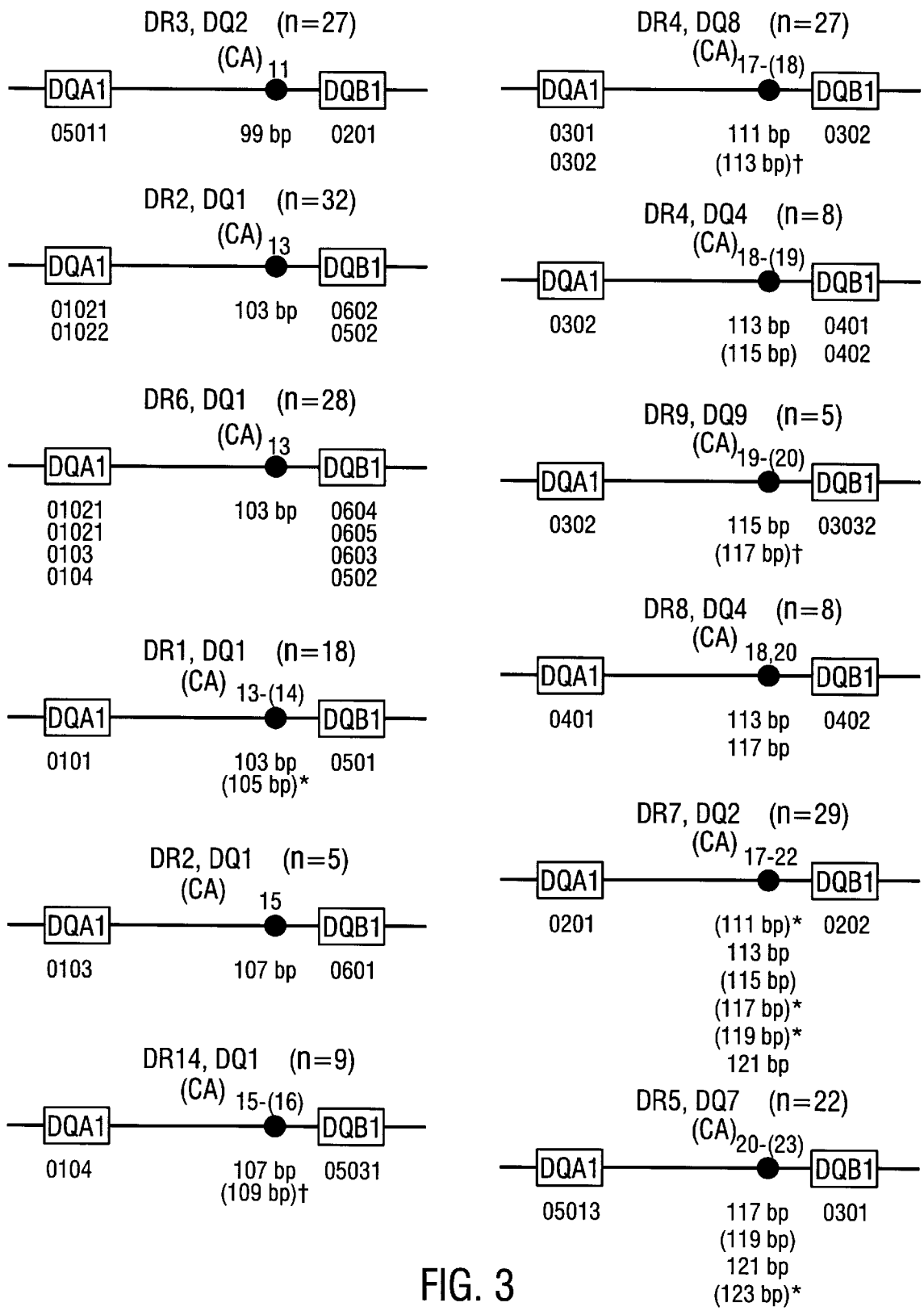
FIG. 3 is a display of the DQCAR polymorphisms observed in a selected set of DQB1/DQA1 haplotypes from the population survey of Example 1.

FIG. 3 is a display of the observed DQCAR polymorphisms in a selected set of DQB1/DQA1 haplotypes from the population survey. DQA1/DQCAR/DQB1 haplotypes are ordered by increasing DQCAR sizes. Only frequent haplotypic combinations in various ethnic groups are included. As oligotyping was not performed on these samples, these were tentatively assigned from known associations (see Table 3 and 5; Fernandez-Vina et al., "Alleles at Four HLA Class II Loci Determined by Oligonucleotide Hybridization and their Association in Five Ethnic Groups," *Immunogenetics* 34:299 (1991); and Kimura et al., "DNA Typing of HLA Class II Genes in B-lymphoblastoid Cell Lines Homozygous for HLA," *Tissue Antigens* 40:5 (1992)).

The symbols in the FIG. 3 are defined as follows: "*" not observed in our panel of oligotyped samples (Table 1) but found in our population survey (Table 5); "†" observed in our panel of oligotyped samples but not in our population survey; and "n" number of haplotypes analyzed in each group. Rare DQCAR allelic combinations are between parenthesis. Haplotypes were considered rare when less than 15% of all haplotypes in the group carried the given DQCAR allele in our multiethnic panel. Note that as the size of the $(CA)_n$ increases, more DQCAR alleles are observed in individual haplotypes.

L. Sunmmary of Conclusions Drawn from Example 1 Characterization of DQCAR in Human Groups In Example 1, the polymorphism of a $(CA)_n$ microsatellite designated DQCAR has been characterized. The DQCAR microsatellite marker is located 1–2 kb telomeric of DQB1 gene and 10 kb centromeric from DQA1. Twelve alleles, based on length polymorphism, were defined. This new marker showed linkage disequilibrium with HLA-DQ and, thus, enabled the demonstration of new haplotypic diversity in the DQ region.

Similar associations between DQ types and DQCAR alleles were found in the four ethnic groups studied (Caucasian-, African-, Mexican, Asian-American). These results suggest that the DQCAR variation observed is older than the emergence of these ethnic groups. This observation agrees with genetic distance analysis, suggesting that a large number of the HLA alleles in contemporary populations are extremely ancient.

A striking result from this characterization was the fact that most DQ1 (DQ5 and DQ6) bearing haplotypes showed the same DQCAR allele. Thirteen DQA1/DQB1 allelic DQ1 combinations were tested and the same DQCAR allele (103), was present in all but three (Table 1 and FIG. 3). In contrast, DQCAR repeat alleles in non-DQ1 haplotypes exhibited much greater diversity. This variation in the DQCAR alleles was observed within the same DRB1-DQA1-DQB1 combination, such as the DR7, DQ2 haplotype in which 3 different DQCAR alleles could be detected, or within the same DQA1/DQB1 combinations, as seen in some DQ7 haplotypes (Table 1 and FIG. 3). A higher degree of diversity in the DQA1 and DQB1 genes exists in the DQ1 as compared to the non-DQ1 associated haplotypes, but much less DQCAR allelic diversity is observed among the DQ1 haplotypes. Therefore, the associations between the DQCAR alleles and the DQ types cannot be explained only by the allelic diversity found in the DQA1 and DQB1 genes themselves.

The polymorphism observed in the DQCAR locus could have been generated by mutation via strand slippage during replication and/or chromosomic crossover within the DQ region. Slippage implies displacement of the DNA strands followed by mispairing of complementary bases at the site of the repeat sequence. The rate of strand slippage has been suggested to be dependent on the length of the dinucleotide sequence, longer sequences being more susceptible. Weber, "Informativeness of Human $(dC-dA)_n \cdot (dG-dT)_n$ Polymorphisms," *Genomics* 7:524 (1990), in a thorough analysis of over 100 human CA repeats has estimated that microsatellite sequences with 10 or fewer repeats were never polymorphic whereas sequences with 16 or more repeats were always moderately to highly polymorphic. Conversely, Valdes et al., "Allele Frequencies at Microsatellite Loci: the Stepwise Mutation Model Revisited," *Genetics* 133:737 (1993), did not find evidence for a correlation between mutation rate and allele size, or between allele number and average allele size. In the Valdes et al. study of 102 microsatellite loci, however, total allele sizes and not number of repeats were analyzed, which introduces another source of variation. In the characterization of this invention, greater DQCAR repeat allelic diversity and thus greater strain slippage in haplotypes with repeats longer than DQCAR 111 (17 CA repeats) were observed. In DQ haplotypes associated with shorter DQCAR alleles, linkage disequilibrium was very strong within any given DQA1/DQB1 cis combination. This is the case for DQCAR 99 and the DR3,DQ2 haplotype, for DQCAR 103 and most of the DQ1 haplotypes, and for DQCAR 111 and the DR4,DQ8 haplotypes. In contrast, DQA1/DQB1 combinations with longer DQCAR alleles show greater diversity at the microsatellite level even when the same DQA1 and DQB1 alleles are involved, as observed in the DR7, DQ2 and DR5, DQ7 haplotypes (see FIG. 3). This could suggest that 2 bp mutant alleles are more easily generated (i.e., produced within shorter evolutionary life spans) among longer DQCAR repeat units.

Diversification events related to the HLA-DQ region could also have contributed to the polymorphism of this microsatellite locus. Recombination within the HLA class II region is haplotype dependent. For instance, ancestral recombinations involving the DR7, DQ3 and DR7, DQ2 haplotypes appear to have been located mostly in the region between DQA1 and DQB1, whereas exchanges between DQ1 and DQ3 haplotypes have occurred mainly between DQA1 and DRB1. The patterns of DRB1-DQA1-DQB1 associations observed in individual haplotypes also suggest that non-DQ1 haplotypes have been subjected to more genetic exchanges within the DQ region than DQ1 haplotypes.

The DQA1/DQB1 alleles of the DQ1 haplotypes are found strictly within the DQ1 family with only one rare haplotype containing a DQ1β with a non-DQ1α allele ever reported.

Merryman et al., "A Novel Association of DQα and DBβ Genes in the DRw10 Haplotype: Determination of a DQw1 Specificity by the DQb-chain," *J. Immunol* 13:2068 (1989). DQA1 and DQB1 alleles may thus have coevolved on individual DQ1 haplotypes. In contrast, DQA1 and DQB1 alleles found in DQ2, DQ3 and DQ4 haplotypes are found across broad DQ specificities. For example, DQA1*0302 and DQA1*0501 can be found in cis with DQB1*03 or *04 (DQ3 and DQ4) and DQB1*02 or DQB1*03 (DQ2 and DQ3) respectively. This suggests frequent intra DQA1/DQB1 cross overs between these haplotypes.

Several factors could explain the fact that DQ1 haplotypes have fewer ancestral recombination sites mapping between the DQA1 and DQB1 loci. Differences in the molecular organization of DQ1 versus non-DQ1 haplotypes could determine preferential recombination sites within HLA haplotypes. Alternatively but not mutually exclusively, some recombinants might be maintained by natural selection, thus favoring specific recombination sites between selected haplotypes. In this regard, the selective pressure needed to keep certain DQA1/DQB1 cis combinations might be a determining factor. At the protein level, Kwok et al., "HLA-DQ Allelic Polymorphisms Constrain Patterns of Class II Heterodimer Formation," *J. Immunol* 150:2263 (1993), found that DQβ and DQα chains from DQ1 specifities could not form stable cell surface heterodimers with DQα or DQβ chains from non-DQ1haplotypes. Therefore, it seems that there is allowable α-β interchange within the DQ1 family of haplotypes, but not between this family and the non-DQ1 haplotypes. Thus, crossover between the non-DQ1 haplotypes would be selected from an evolutionary standpoint because they result more often in functional heterodimers.

This restriction in recombination appears reflected in the HLA-DQ/DQCAR haplotypes found in this study. Genetic exchanges between DQCAR and DQA1 or DQB1 are likely to have occurred among non-DQ1 haplotypes. These recombinations could thus have increased DQ/CAR haplotypic diversity as many different DQCAR alleles are found in these haplotypes. The DQCAR alleles found are also large and possibly both genetic exchanges and strand slippage have contributed to the increased diversity observed in non-DQ1 haplotypes. For DQ1 haplotypes, either recombination between DQA1 and DQB1 is rare or it only occurs within the DQ1 family thus maintaining the DQCAR 103 allele in most cases. Together with the fact that the DQCAR 103 allele is short and less subject to mutation, this would account for the lower degree of polymorphism observed in DQ1 haplotypes.

In conclusion, analysis of the pattern of linkage disequilibrium between DQCAR and DQ alleles suggests that longer DQCAR alleles could have higher mutation rates. Haplotype dependent recombination in the HLA class II region may have also contributed to the haplotype diversity observed in this study. The polymorphism of this microsatellite could also be used to better define disease association with HLA-DQ. Since more haplotypic diversity is observed with this microsatellite, studying this marker could be helpful in determining if the DQA1 and DQB1 genes themselves, or a yet unknown gene linked to HLA, are involved in disease susceptibility.

EXAMPLE 2

Method of DQCAR Typing an Individual

As an example of how an individual is typed with the present microsatellite markers, a method for DQCAR typing an individual involves:

obtaining a sample of nucleic acid from an individual;
amplifying the nucleic acid sample with at least two primers selected from CAR1, CAR2, and complementary sequences of CAR1 and CAR2; and
detecting the DQCAR allele in the sample by measuring the length of said amplified extension products and correlating said length to a DQCAR allele.

For example, DQCAR can be used as a marker to test zygosity in twin pairs. The marker can also be used to differentiate and thus identify samples from two unrelated individuals.

In this example, the test will be used for identifying two samples of human tissue to test if they come from the same individual. DNA will be extracted and purified by conventional methods, or PCR amplification could be done directly using the tissue sample in appropriate solutions. PCR amplification of DQCAR will be done as indicated in Example 1, the resulting product being run onto a gel. This result is determined by observing the pattern of DQCAR, for example, on the sequence gel. If the patterns for the two samples are identical, that would suggest the two tissues come from the same individual. This test may be performed, if necessary, with other marker tests to further define the probable identity of the samples.

EXAMPLE 3

Characterization of DQCAR, DQCARII, and G51152

The characterization of the DQCAR, DQCARII, and G51152 microsatellite markers was performed on 78 Tenth International Histocompatibility Workshop B cell lines and more than 1,000 control Japanese, New Guinean, and Caucasian samples which had been previously oligotyped by conventional methods. Tables 6–9 show the results obtained when haplotypes were determined on the cell lines and control samples using these three microsatellite markers.

In Table 6, DRB1, DQA1, DQCARII, DQCAR, DQB1, and G51152 haplotypes observed in a panel of B-cell lines characterized at the HLA class II level (10th workshop B-cell lines panel) are reported. DRB1, DQA1, DQCARII, DQCAR, DQB1, and G51152 control haplotypes observed in 718 normal Japanese, 99 normal Norwegian and 95 New Guineans are reported in Table 7, 8 and 9 respectively. In all cases, specific DRB1, DQA1, DQCARII, DQCAR, DQB1, and G5115 haplotypes could be deduced from the genotyping information, thus describing existing normal haplotypes and their frequency in each population.

The significant association between DQCAR, DQCARII, and G51152 allele lengths and specific HLA DQ alleles indicates that these markers can be useful for predicting HLA DQA1 and DQB1 type. Indirect information is also suggested for DRB1 in many cases, but additional microsatellites may have to be typed in this region to establish a stronger association with DRB1 loci.

Figure 4:
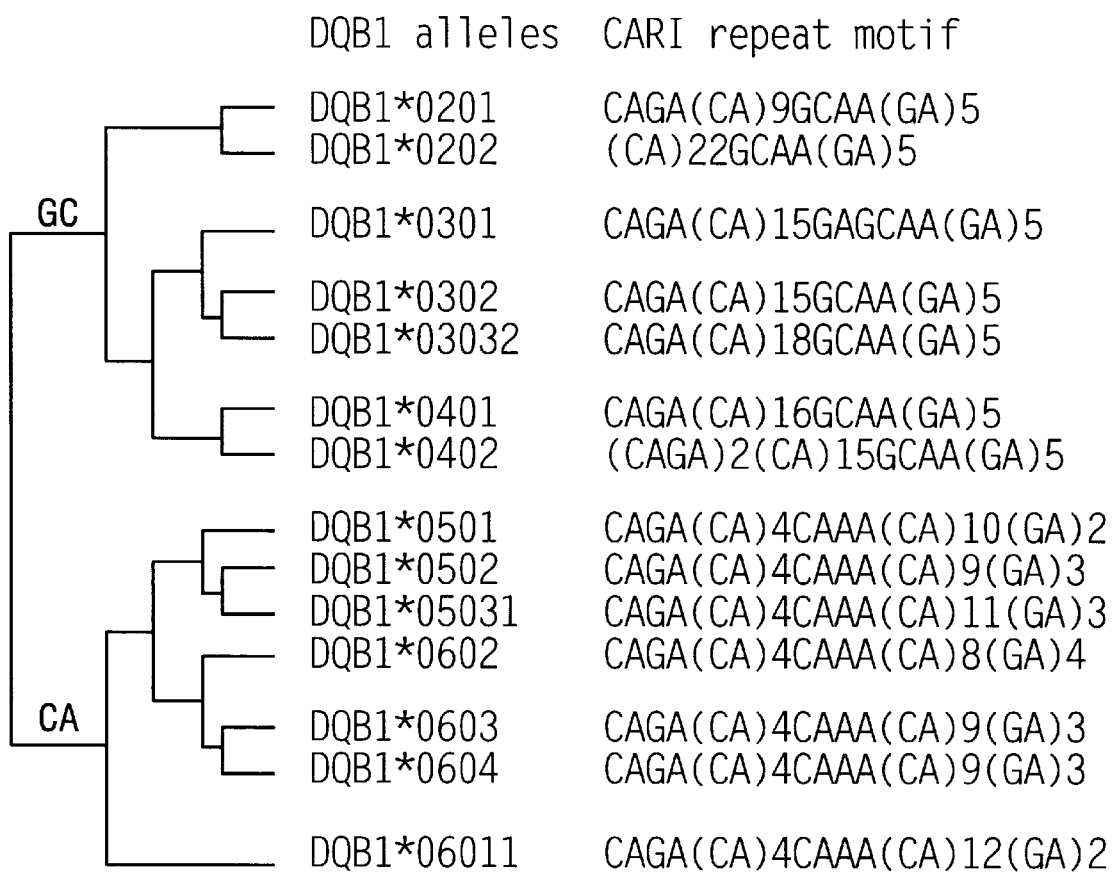
FIG. 4 demonstrates the association between DQCAR allele sequencing and DQB1 alleles. The phylogenetic relationships between DQB1 and DQCAR allele sequences are reported. DQB1 alleles were grouped into two major clusters using Neighbor Joining method (DQ1 and non-DQ1 alleles). DQCAR data indicates two distinct sequence patterns that have a tight relationship with the DQB1 phylogeny, despite differing numbers of CA repeats.
Figure 5:
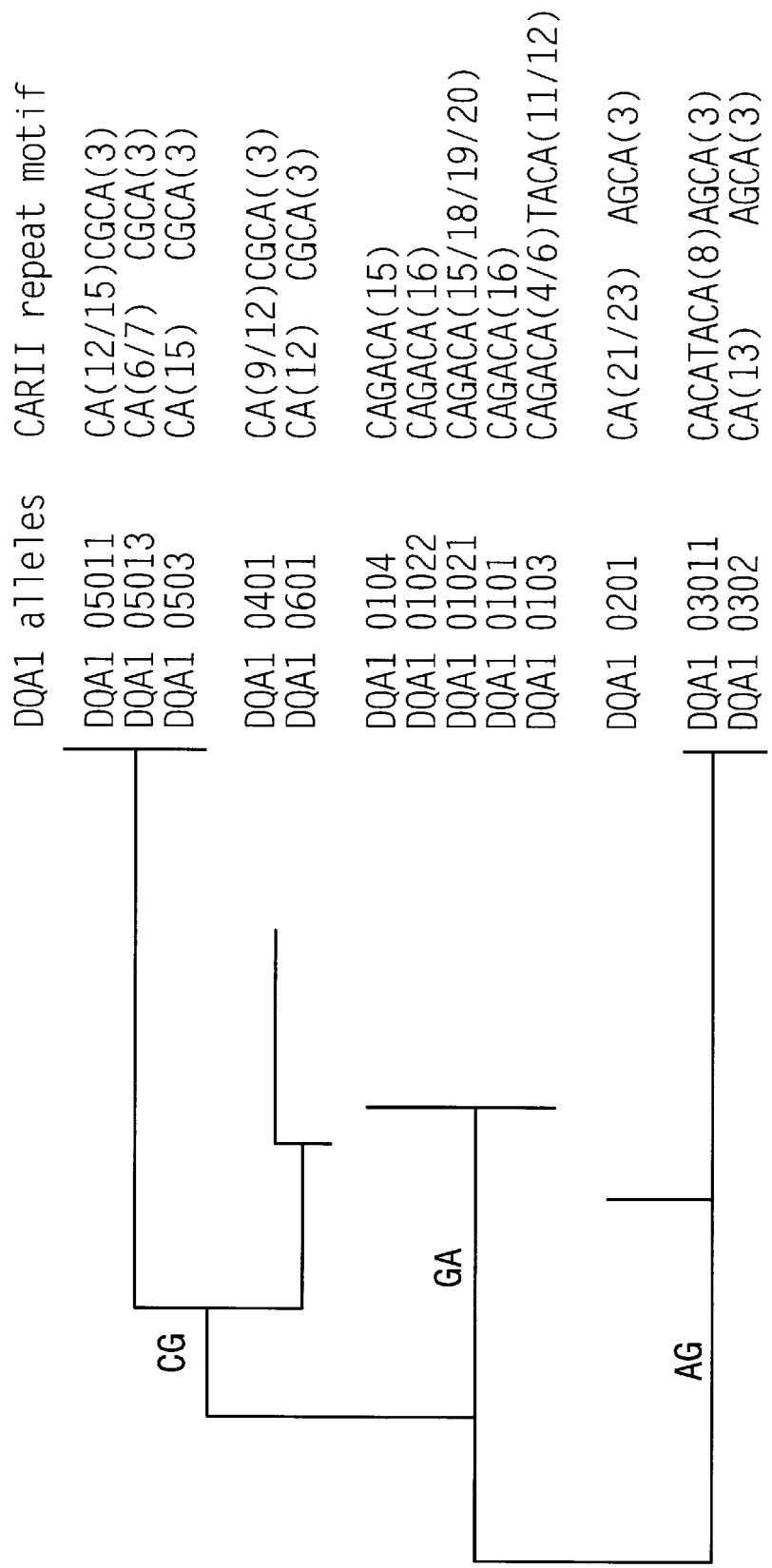
FIG. 5 demonstrates the association between DQCARII allele sequencing and DQA1 alleles. The phylogenetic relationships between individual DQA1 and DQCARII allele sequences are reported. DQA1 alleles were grouped into three major clusters. DQCARII alleles show three distinct sequence patterns associated with the three DQA1 clusters.

Sequencing of the DQCAR, DQCARII, and G51152 loci was also performed on a number of samples, and correlations were drawn with the HLA DQA1 and DQB1 phylogenetic tree. In all cases, DQCAR sequencing was found to correlate with DQB1 alleles (FIG. 4) whereas DQCARII allele sequencing was found to correlate with DQA1 (FIG. 5). The sequencing of G51152 did not correlate perfectly with the DQB1 phylogenetic tree, however, the information provided did slightly improve the overall predictability for HLA typing. Allele-specific sequence information could also be used to increase typing resolution and accuracy since this provides the basis for distinguishing alleles of the same length which have sequence polymorphisms.

EXAMPLE 4

Method of High Resolution HLA DQA1 and HLA DQB1 Typing

To test the feasibility of using the information obtained from typing the DQCAR, DQCARII, and G51152 microsatellites in predicting HLA DQ type, a simple computer program was developed. This program uses only the ethnic group of the subject and the genotyping results for these three markers. Table 10 demonstrates that this approach can indeed predict DQA1 and DQB1 type with very high accuracy. Overall predictability ranges from 93–100%. Predicability was outstanding in all cases with the exception of a few alleles, DQA1*03, DQB1*0302, DQB1*04. These results compare well with established HLA class II typing techniques. It is believed that prediction accuracy will be improved further upon additional characterization and optimization.

EXAMPLE 5

Method for Detecting an Individual's Susceptibility to an HLA Disease

DQCAR is an HLA marker that can provide information regarding an individual's predisposition, or susceptibility, to an autoimmune disease. In this example, an individual would like to know if he is predisposed to a disease involving specific HLA types. DQCAR typing will be performed on a tissue sample from the individual. The resulting DQCAR information can be interpreted (with or without additional HLA typing information) to answer his question by looking at how specific DQCAR alleles are associated with specific HLA types (see Example 1 characterization of the DQCAR marker).

In a preferred embodiment, the steps of the method for detecting an individual's susceptibility to an HLA disease, such as an autoimmune disease, can be described as first determining a characterization of the $(CA)_n$ repeat unit in the region between HLA DQA1 and DQB1 (DQCAR), as in Example 1, comprising the steps of:

(i) extracting DNA from a sample to be tested;
(ii) amplifying the $(CA)_n$ repeat unit located between HLA DQA1 and DQB 1;
(iii) detecting the DQCAR allele in the sample;
(iv) determining the HLA-DR and -DQ type of the sample;
(v) repeating steps (i) through (iv) for a statistically significant number of samples; and (vi) determining the identity and frequency of the DQCAR alleles and the linkage disequilibrium between HLA DQ, HLA DR, and DQCAR. This characterization is then compared to the occurrence of a subject disease to determine the extent of any relationship, or association, between the characterization and the subject disease. If the individual's DQCAR type matches a DQCAR type determined to be associated with a particular HLA type and/or disease, that individual may be susceptible to obtaining that disease.

In a preferred embodiment, the amplification of step (ii) is performed by PCR using the primers CAR1 and CAR2. In a further preferred embodiment, CAR1 and CAR2 are, respectively, SEQ ID NO. 1 and SEQ ID NO. 2.

EXAMPLE 6

Method Of Assessing Disease Susceptibility to IDDM Using DQCAR Typing

DQCAR allele frequencies in Japanese insulin-dependent diabetes mellitus (IDDM) patients and Japanese, New Guinean, and Caucasian controls were determined in order to explore the value of DQCAR typing to detect HLA associated disease (Table 11). As expected from the strong association between DQCAR alleles and HLA DQ alleles, significant differences in DQCAR allele frequencies were identified between control and disease individuals. The data presented in Table 11 clearly demonstrates that DQCAR allele length can effectively differentiate between IDDM patients and controls, thereby providing a method whereby susceptibility to IDDM could be predicted based upon DQCAR allele length. It is expected that the use of typing information from markers in addition to DQCAR will further strengthen the ability to assess IDDM susceptibility. In addition, this example can be easily generalized to other HLA associated diseases through the use of other microsatellite markers in the HLA region which are in strong association with specific HLA alleles.

EXAMPLE 7

Method for Determining the Suitability of Donors for Tissue or Organ Transplantation HLA matching for prospective donors and recipients of tissue or organ transplantation is very important for the success of the transplantation. DQCAR, DQCARII, and G51152 could be used to further test HLA identity between a prospective donor and recipient in the class II regions. Indeed, different alleles might detect additional HLA class II diversity that are not yet known. The test is relatively easy, quick and inexpensive to perform. It could also be a way to quickly test blood relatives of the patient to be transplanted to determine whether they carry the same HLA haplotype.

In this example, tissue from the prospective donor and recipient will be typed with DQCAR, DQCARII, and G51152. Only prospective donors with a similar typing pattern will then be subjected to more HLA testing and possibly ultimately involved in the transplantation process.

In a preferred embodiment, the method of determining the suitability of a donor for tissue or organ transplantation, such as bone marrow transplantation, comprises performing the typing process, as in Example 6, to determine the alleles present in the DNA of the prospective donor tissue. The typing process is also performed to determine the alleles present in the DNA of the prospective recipient tissue. The alleles of the respective samples are then compared. If the types are the same, the prospective donor and recipient match in at least one significant category and the recipient and candidate donor may be considered for further testing.

Additional advantages and modifications will be readily apparent to those skilled in the art. The invention in its broader aspects is therefore not limited to the specific details or representative examples described. Accordingly, departures may be made from the detail without departing from the spirit or scope of the disclosed general inventive concept.

TABLE 6

Haplotypes found in B cell lines

| NO. | WS # | DRB1 | DRB1 | DQA1 | DQA1 | CAR II | CAR II | CAR I | CAR I | DQB1 | DQB1 | G51152 | G51152 |
| --- | --- | --- | --- | --- | --- | --- | --- | --- | --- | --- | --- | --- | --- |
| 1 | 9003 | 0101 | 0101 | 0101 | 0101 | 202 | 202 | 103 | 103 | 0501 | 0501 | 214 | 214 |
| 2 | 9004 | 0101 | 0101 | 0101 | 0101 | 202 | 202 | 103 | 103 | 0501 | 0501 | 244 | 244 |
| 3 | 9005 | 0101 | 0101 | 0101 | 0101 | 202 | 202 | 103 | 103 | 0501 | 0501 | 244 | 244 |
| 4 | 9006 | 0101 | 0101 | 0101 | 0101 | 202 | 202 | 103 | 103 | 0501 | 0501 | 244 | 244 |
| 5 | 9080 | 0101 | 0101 | 0101 | 0101 | 202 | 202 | 103 | 103 | 0501 | 0501 | 244 | 244 |
| 6 | 9002 | 0102 | 0102 | 0101 | 0101 | 202 | 202 | 103 | 103 | 0501 | 0501 | 226 | 226 |
| 7 | 9078 | 0102 | 0102 | 0101 | 0101 | 202 | 202 | 103 | 103 | 0501 | 0501 | 226 | 226 |
| 8 | 9010 | 1501 | 1501 | 01021 | 01021 | 200 | 200 | 103 | 103 | 0602 | 0602 | 222 | 222 |
| 9 | 9013 | 1501 | 1501 | 01021 | 01021 | 200 | 202 | 103 | 103 | 0602 | 0602 | 222 | 222 |
| 10 | 9014 | 1501 | 1501 | 01021 | 01021 | 200 | 200 | 103 | 103 | 0602 | 0602 | 222 | 222 |
| 11 | 9017 | 1501 | 1501 | 01021 | 01021 | 200 | 200 | 103 | 103 | 0602 | 0602 | 222 | 222 |
| 12 | 9081 | 1501 | 1501 | 01021 | 01021 | 200 | 200 | 103 | 103 | 0602 | 0602 | 222 | 222 |
| 13 | 9082 | 1501 | 1501 | 01021 | 01021 | 200 | 200 | 103 | 103 | 0602 | 0602 | 222 | 222 |
| 14 | 9083 | 1501 | 1501 | 01021 | 01021 | 200 | 200 | 103 | 103 | 0602 | 0602 | 222 | 222 |
| 15 | 9011 | 1502 | 1502 | 0103 | 0103 | 206 | 206 | 107 | 107 | 06011 | 06011 | 214 | 214 |
| 16 | 9012 | 1601 | 1601 | 01022 | 01022 | 202 | 202 | 103 | 103 | 0502 | 0502 | 214 | 214 |
| 17 | 9084 | 1601 | 1601 | 01022 | 01022 | 202 | 202 | 103 | 103 | 0502 | 0502 | 214 | 214 |
| 18 | 9016 | 1602 | 1602 | 0501 | 0501 | 186 | 186 | 115 | 115 | 0301 | 0301 | 214 | 214 |
| 19 | 9018 | 0301 | 0301 | 05011 | 05011 | 198 | 198 | 99 | 99 | 0201 | 0201 | 216 | 216 |
| 20 | 9019 | 0301 | 0301 | 05011 | 05011 | 198 | 198 | 99 | 99 | 0201 | 0201 | 216 | 216 |
| 21 | 9020 | 0301 | 0301 | 05011 | 05011 | 198 | 198 | 99 | 99 | 0201 | 0201 | 216 | 216 |
| 22 | 9022 | 0301 | 0301 | 05011 | 05011 | 204 | 204 | 99 | 99 | 0201 | 0201 | 216 | 216 |
| 23 | 9023 | 0301 | 0301 | 05011 | 05011 | 204 | 204 | 99 | 99 | 0201 | 0201 | 216 | 216 |
| 24 | 9086 | 0301 | 0301 | 05011 | 05011 | 204 | 204 | 99 | 99 | 0201 | 0201 | 216 | 216 |
| 25 | 9087 | 0301 | 0301 | 05011 | 05011 | 204 | 204 | 99 | 99 | 0201 | 0201 | 216 | 216 |
| 26 | 9088 | 0301 | 0301 | 05011 | 05011 | 204 | 204 | 99 | 99 | 0201 | 0201 | 216 | 216 |

TABLE 6-continued

Haplotypes found in B cell lines

| NO. | WS # | DRB1 | DRB1 | DQA1 | DQA1 | CAR II | CAR II | CAR I | CAR I | DQB1 | DQB1 | G51152 | G51152 |
|---|---|---|---|---|---|---|---|---|---|---|---|---|---|
| 27 | 9021 | 0302 | 0302 | 0401 | 0401 | 198 | 198 | 117 | 117 | 0402 | 0402 | 226 | 226 |
| 28 | 9007 | 0401 | 1602 | 01022 | 0301 | 194 | 204 | 103 | 111 | 0502 | 0302 | 214 | 226 |
| 29 | 9025 | 0401 | 0401 | 0302 | 0302 | 194 | 194 | 117 | 117 | 0301 | 0301 | 214 | 214 |
| 30 | 9029 | 0401 | 0401 | 0301 | 0301 | 194 | 194 | 111 | 111 | 0302 | 0302 | 226 | 226 |
| 31 | 9031 | 0401 | 0401 | 0301 | 0301 | 194 | 194 | 111 | 111 | 0302 | 0302 | 226 | 226 |
| 32 | 9032 | 0401 | 0401 | 0301 | 0301 | 194 | 194 | 111 | 111 | 0302 | 0302 | 226 | 226 |
| 33 | 9034 | 0401 | 0401 | 0302 | 0302 | 194 | 194 | 111 | 111 | 0302 | 0302 | 226 | 226 |
| 34 | 9026 | 0402 | 0402 | 0301 | 0301 | 200 | 200 | 111 | 111 | 0302 | 0302 | 226 | 226 |
| 35 | 9028 | 0404 | 0404 | 0301 | 0301 | 194 | 194 | 111 | 111 | 0302 | 0302 | 226 | 226 |
| 36 | 9092 | 0404 | 0404 | 0301 | 0301 | 194 | 194 | 111 | 111 | 0302 | 0302 | 226 | 226 |
| 37 | 9107 | 0405 | 0405 | 0302 | 0302 | 194 | 194 | 115 | 115 | 0401 | 0401 | 226 | 226 |
| 38 | YAS | 0405 | 0410 | 0302 | 0302 | 194 | 194 | 113 | 115 | 0401 | 0402 | 226 | 226 |
| 39 | 9030 | 0407 | 0407 | 0301 | 0301 | 194 | 194 | 119 | 119 | 0301 | 0301 | 214 | 214 |
| 40 | 9035 | 1101 | 1101 | 05013 | 05013 | 188 | 188 | 121 | 121 | 0301 | 0301 | 214 | 214 |
| 41 | 9036 | 1101 | 1101 | 01022 | 01022 | 202 | 202 | 103 | 103 | 0502 | 0502 | 214 | 214 |
| 42 | 9037 | 1101 | 1101 | 05013 | 05013 | 188 | 188 | 121 | 121 | 0301 | 0301 | 214 | 214 |
| 43 | 9043 | 1101 | 1101 | 05013 | 05013 | 188 | 188 | 121 | 121 | 0301 | 0301 | 214 | 214 |
| 44 | 9039 | 1102 | 1102 | 05013 | 05013 | 188 | 188 | 121 | 121 | 0301 | 0301 | 214 | 214 |
| 45 | 9040 | 1102 | 1102 | 05013 | 05013 | 186 | 186 | 117 | 117 | 0301 | 0301 | 214 | 214 |
| 46 | 9042 | 1103 | 1103 | 05013 | 05013 | 188 | 188 | 121 | 121 | 0301 | 0301 | 214 | 214 |
| 47 | 9045 | 1104 | 1201 | 05013 | 05013 | 186 | 188 | 121 | 117 | 0301 | 0301 | 214 | 214 |
| 48 | 9089 | 1104 | 1104 | 05013 | 05013 | 188 | 188 | 121 | 121 | 0301 | 0301 | 214 | 214 |
| 49 | 9058 | 1301 | 1301 | 0103 | 0103 | 208 | 208 | 103 | 103 | 0603 | 0603 | 222 | 222 |
| 50 | 9060 | 1301 | 1301 | 0103 | 0103 | 208 | 208 | 103 | 103 | 0603 | 0603 | 222 | 222 |
| 51 | 9062 | 1301 | 1301 | 0103 | 0103 | 208 | 208 | 103 | 103 | 0603 | 0603 | 222 | 222 |
| 52 | 9065 | 1301 | 1301 | 0103 | 0103 | 208 | 208 | 103 | 103 | 0603 | 0603 | 222 | 222 |
| 53 | 9055 | 1302 | 1302 | 01021 | 01021 | 206 | 206 | 103 | 103 | 0609 | 0609 | 222 | 222 |
| 54 | 9056 | 1302 | 1401 | 01021 | 0104 | 200 | 208 | 103 | 107 | 05031 | 0604 | 220 | 218 |
| 55 | 9063 | 1302 | 1302 | 01021 | 01021 | 210 | 210 | 103 | 103 | 0604 | 0604 | 220 | 220 |
| 56 | 9097 | 1302 | 1302 | 01021 | 01021 | 210 | 214 | 103 | 103 | 0604 | 0604 | 220 | 220 |
| 57 | 9054 | 1401 | 1401 | 0104 | 0104 | 200 | 200 | 107 | 107 | 05031 | 05031 | 218 | 218 |
| 58 | 9057 | 1401 | 1401 | 0104 | 0104 | 200 | 200 | 107 | 107 | 05031 | 05031 | 218 | 218 |
| 59 | 9061 | 1401 | 1401 | 0104 | 0104 | 200 | 200 | 107 | 107 | 05031 | 05031 | 214 | 214 |
| 60 | 9064 | 1402 | 1402 | 0503 | 0503 | 202 | 202 | 117 | 117 | 0301 | 0301 | 226 | 226 |
| 61 | 9099 | 1402 | 1402 | 0502 | 0502 | 204 | 204 | 117 | 117 | 0301 | 0301 | 214 | 214 |
| 62 | 9047 | 0701 | 0701 | 0201 | 0201 | 218 | 218 | 113 | 113 | 0202 | 0202 | 214 | 214 |
| 63 | 9048 | 0701 | 0701 | 0201 | 0201 | 218 | 218 | 113 | 113 | 0202 | 0202 | 214 | 214 |
| 64 | 9051 | 0701 | 0701 | 0201 | 0201 | 218 | 218 | 121 | 121 | 0202 | 0202 | 214 | 214 |
| 65 | 9052 | 0701 | 0701 | 0201 | 0201 | 214 | 214 | 119 | 119 | 03032 | 03032 | 214 | 214 |
| 66 | 9093 | 0701 | 0701 | 0201 | 0201 | 218 | 220 | 113 | 113 | 0202 | 0202 | 214 | 214 |
| 67 | 9094 | 0701 | 0701 | 0201 | 0201 | 218 | 218 | 115 | 115 | 0202 | 0202 | 214 | 214 |
| 68 | 9095 | 0701 | 0701 | 0201 | 0201 | 214 | 218 | 117 | 119 | 0202 | 03032 | 214 | 214 |
| 69 | 9106 | 0701 | 0701 | 0201 | 0201 | 214 | 218 | 121 | 121 | 0202 | 03032 | 214 | 214 |
| 70 | 9067 | 0801 | 0801 | 0401 | 0401 | 198 | 198 | 113 | 113 | 0402 | 0402 | 194 | 194 |
| 71 | 9068 | 0801 | 0801 | 0401 | 0401 | 198 | 198 | 113 | 113 | 0402 | 0402 | 194 | 194 |
| 72 | 9069 | 0801 | 0801 | 0401 | 0401 | 198 | 198 | 113 | 113 | 0402 | 0402 | 194 | 194 |
| 73 | 9071 | 0802 | 0802 | 0401 | 0401 | 198 | 198 | 117 | 117 | 0402 | 0402 | 226 | 226 |
| 74 | 9072 | 0802 | 0802 | 0401 | 0401 | 198 | 198 | 117 | 117 | 0402 | 0402 | 226 | 226 |
| 75 | 9066 | 08032 | 08032 | 0103 | 0103 | 206 | 206 | 107 | 107 | 06011 | 06011 | 214 | 214 |
| 76 | 9070 | 08032 | 08032 | 0601 | 0601 | 198 | 198 | 113 | 113 | 0301 | 0301 | 214 | 214 |
| 77 | 9075 | 0901 | 0901 | 0302 | 0302 | 198 | 198 | 117 | 117 | 03032 | 03032 | 214 | 214 |
| 78 | 9076 | 0901 | 0901 | 0302 | 0302 | 198 | 198 | 115 | 115 | 03032 | 03032 | 214 | 214 |

TABLE 7

Haplotypes found in 718 Japanese subjects

| NO | DRB1 | DQA1 | CAR II | CAR I | DQB1 | G51152 | No of H |
|---|---|---|---|---|---|---|---|
| 1 | 0101 | 0101 | 202 | 103 | 0501 | 244 | 101 |
| 2 | 1501 | 01021 | 200 | 103 | 0502 | 214 | 1 |
| 3 | 1501 | 01021 | 200 | 107 | 06011 | 214 | 1 |
| 4 | 1501 | 01021 | 198 | 103 | 0602 | 220 | 1 |
| 5 | 1501 | 01021 | 200 | 103 | 0602 | 220 | 88 |
| 6 | 1501 | 05013 | 186 | 117 | 0301 | 214 | 5 |
| 7 | 1501 | 05013 | 186 | 121 | 0301 | 214 | 2 |
| 8 | 1502 | 0103 | 206 | 107 | 06011 | 214 | 168 |
| 9 | 1502 | 0103 | 206 | 109 | 06011 | 214 | 1 |
| 10 | 1502 | 01021 | 200 | 103 | 0602 | 220 | 2 |
| 11 | 1502 | 01022 | 202 | 103 | 0502 | 214 | 2 |
| 12 | 1602 | 01022 | 202 | 103 | 0502 | 214 | 6 |
| 13 | 1602 | 0103 | 206 | 107 | 06011 | 214 | 2 |
| 14 | 0301 | 05011 | 198 | 99 | 0201 | 216 | 5 |
| 15 | 0301 | 05011 | 200 | 99 | 0201 | 216 | 2 |
| 16 | 0401 | 0302 | 194 | 117 | 0301 | 214 | 22 |
| 17 | 0403 | 0301 | 194 | 111 | 0302 | 226 | 12 |
| 18 | 0403 | 0301 | 194 | 113 | 0302 | 226 | 21 |
| 19 | 0404 | 0301 | 194 | 113 | 0302 | 226 | 3 |
| 20 | 0405 | 0301 | 194 | 113 | 0302 | 226 | 2 |
| 21 | 0405 | 0302 | 194 | 113 | 0302 | 226 | 1 |
| 22 | 0405 | 0302 | 194 | 117 | 03032 | 214 | 1 |
| 23 | 0405 | 0302 | 194 | 111 | 0401 | 226 | 5 |
| 24 | 0405 | 0302 | 194 | 113 | 0401 | 226 | 110 |

TABLE 7-continued

Haplotypes found in 718 Japanese subjects

| NO | DRB1 | DQA1 | CAR II | CAR I | DQB1 | G51152 | No of H |
|---|---|---|---|---|---|---|---|
| 25 | 0405 | 0302 | 194 | 115 | 0401 | 226 | 63 |
| 26 | 0405 | 0302 | 194 | 117 | 0401 | 226 | 11 |
| 27 | 0406 | 0301 | 194 | 109 | 0302 | 226 | 1 |
| 28 | 0406 | 0301 | 194 | 111 | 0302 | 226 | 40 |
| 29 | 0406 | 0301 | 194 | 115 | 0302 | 226 | 6 |
| 30 | 0407 | 0301 | 194 | 111 | 0302 | 226 | 5 |
| 31 | 0407 | 0301 | 194 | 113 | 0302 | 226 | 3 |
| 32 | 0409 | 0302 | 194 | 115 | 0401 | 226 | 1 |
| 33 | 0410 | 0302 | 194 | 113 | 0402 | 226 | 18 |
| 34 | 0410 | 0302 | 194 | 113 | 0402 | 248 | 1 |
| 35 | 0410 | 0302 | 194 | 115 | 0402 | 226 | 8 |
| 36 | 1101 | 05013 | 188 | 111 | 0302 | 226 | 2 |
| 37 | 1101 | 05013 | 198 | 115 | 03032 | 214 | 1 |
| 38 | 1101 | 05013 | 188 | 113 | 0301 | 214 | 1 |
| 39 | 1101 | 05013 | 188 | 113 | 0302 | 226 | 1 |
| 40 | 1101 | 05013 | 188 | 117 | 0301 | 214 | 1 |
| 41 | 1101 | 05013 | 188 | 121 | 0301 | 214 | 18 |
| 42 | 1101 | 05013 | 188 | 123 | 0301 | 214 | 4 |
| 43 | 1101 | 05013 | 188 | 127 | 0301 | 214 | 1 |
| 44 | 1201 | 0503 | 204 | 117 | 0301 | 214 | 2 |
| 45 | 1201 | 05013 | 186 | 113 | 0302 | 226 | 1 |
| 46 | 1201 | 0301 | 194 | 113 | 0302 | 226 | 2 |
| 47 | 1201 | 0302 | 198 | 115 | 0301 | 214 | 2 |
| 48 | 1201 | 05013 | 186 | 117 | 0301 | 214 | 17 |
| 49 | 1201 | 05013 | 186 | 121 | 0301 | 214 | 13 |
| 50 | 1201 | 05013 | 186 | 123 | 0301 | 214 | 4 |
| 51 | 1201 | 0302 | 198 | 115 | 03032 | 214 | 4 |
| 52 | 12021 | 0601 | 198 | 113 | 0301 | 214 | 1 |
| 53 | 12021 | 0601 | 198 | 113 | 0301 | 192 | 16 |
| 54 | 12021 | 0601 | 200 | 113 | 0301 | 192 | 2 |
| 55 | 1301 | 0103 | 208 | 103 | 0603 | 222 | 6 |
| 56 | 1301 | 0103 | 208 | 103 | 0603 | 224 | 1 |
| 57 | 1301 | 0103 | 208 | 107 | 06011 | 214 | 1 |
| 58 | 1302 | 01021 | 208 | 103 | 0604 | 218 | 1 |
| 59 | 1302 | 01021 | 208 | 103 | 0604 | 220 | 91 |
| 60 | 1302 | 01021 | 206 | 103 | 0609 | 222 | 9 |
| 61 | 1401 | 0104 | 200 | 103 | 0502 | 214 | 18 |
| 62 | 1401 | 0104 | 200 | 107 | 05031 | 218 | 15 |
| 63 | 1402 | 0503 | 204 | 117 | 0301 | 214 | 3 |
| 64 | 1403 | 0503 | 202 | 117 | 0301 | 214 | 2 |
| 65 | 1403 | 0503 | 204 | 113 | 0301 | 214 | 1 |
| 66 | 1403 | 0503 | 204 | 117 | 0301 | 214 | 17 |
| 67 | 1403 | 0503 | 206 | 117 | 0301 | 214 | 1 |
| 68 | 1405 | 0104 | 200 | 107 | 05031 | 218 | 12 |
| 69 | 1405 | 0104 | 200 | 109 | 05031 | 218 | 8 |
| 70 | 1405 | 0104 | 200 | 113 | 05031 | 218 | 1 |
| 71 | 1406 | 0503 | 202 | 117 | 0301 | 214 | 1 |
| 72 | 1406 | 0503 | 204 | 117 | 0301 | 214 | 13 |
| 73 | 1406 | 0503 | 206 | 117 | 0301 | 214 | 1 |
| 74 | 1407 | 0104 | 200 | 107 | 05031 | 218 | 1 |
| 75 | 0701 | 0201 | 218 | 113 | 0202 | 214 | 3 |
| 76 | 0802 | 0301 | 194 | 113 | 0302 | 226 | 26 |
| 77 | 0802 | 0301 | 194 | 115 | 0302 | 226 | 1 |
| 78 | 0802 | 0401 | 194 | 117 | 0402 | 226 | 1 |
| 79 | 0802 | 0401 | 198 | 111 | 0302 | 226 | 1 |
| 80 | 0802 | 0401 | 198 | 111 | 0402 | 226 | 1 |
| 81 | 0802 | 0401 | 198 | 113 | 0402 | 226 | 3 |
| 82 | 0802 | 0401 | 198 | 115 | 0402 | 226 | 4 |
| 83 | 0802 | 0401 | 198 | 117 | 0402 | 226 | 5 |
| 84 | 0802 | 0401 | 200 | 111 | 0302 | 226 | 8 |
| 85 | 0802 | 0401 | 200 | 113 | 0402 | 226 | 1 |
| 86 | 0802 | 0401 | 200 | 115 | 0402 | 226 | 1 |
| 87 | 0802 | 0601 | 198 | 117 | 0402 | 226 | 1 |
| 88 | 08032 | 0103 | 206 | 107 | 06011 | 214 | 126 |
| 89 | 08032 | 0103 | 206 | 107 | 06011 | 216 | 8 |
| 90 | 0901 | 0302 | 198 | 111 | 03032 | 214 | 1 |
| 91 | 0901 | 0302 | 198 | 113 | 03032 | 214 | 4 |
| 92 | 0901 | 0302 | 198 | 115 | 03032 | 214 | 181 |
| 93 | 0901 | 0302 | 198 | 117 | 03032 | 214 | 34 |
| 94 | 0901 | 0302 | 198 | 119 | 03032 | 214 | 3 |
| 95 | 0901 | 0302 | 198 | 121 | 0301 | 214 | 1 |
| 96 | 1001 | 0105 | 198 | 103 | 0501 | 226 | 5 |
| | | | | | | Total | 1436 |

No. of H = number of haplotypes observed

TABLE 8

Haplotypes found in 99 Norwegian subjects

| No. | DRB1 | DQA1 | CAR II | CAR I | DQB1 | G51152 | No. of H |
|---|---|---|---|---|---|---|---|
| 1 | 0101 | 0101 | 202 | 103 | 0501 | 244 | 13 |
| 2 | 0102 | 0101 | 202 | 103 | 0501 | 226 | 2 |
| 3 | 0103 | 0101 | 202 | 103 | 0501 | 244 | 2 |
| 4 | 0104 | 0101 | 202 | 103 | 0501 | 244 | 1 |
| 5 | 1501 | 01021 | 200 | 103 | 0602 | 222 | 26 |
| 6 | 0301 | 05011 | 204 | 99 | 0201 | 216 | 26 |
| 7 | 0401 | 0301 | 194 | 111 | 0302 | 226 | 14 |
| 8 | 0401 | 0302 | 194 | 111 | 0302 | 226 | 1 |
| 9 | 0401 | 0302 | 194 | 117 | 0301 | 214 | 10 |
| 10 | 0401 | 0301 | 194 | 107 | 0302 | 226 | 1 |
| 11 | 0401 | 0301 | 194 | 111 | 0302 | 226 | 1 |
| 12 | 0403 | 0301 | 194 | 111 | 0302 | 226 | 2 |
| 13 | 0404 | 0301 | 194 | 111 | 0302 | 226 | 5 |
| 14 | 0407 | 0302 | 194 | 117 | 0301 | 214 | 2 |
| 15 | 0407 | 0302 | 194 | 119 | 0301 | 214 | 2 |
| 16 | 1101 | 05013 | 188 | 121 | 0301 | 214 | 6 |
| 17 | 1101 | 05013 | 188 | 123 | 0301 | 214 | 1 |
| 18 | 1101 | 05013 | 188 | 125 | 0301 | 214 | 1 |
| 19 | 1102 | 05013 | 188 | 121 | 0301 | 214 | 3 |
| 20 | 1201 | 05013 | 186 | 117 | 0301 | 214 | 5 |
| 21 | 1201 | 05013 | 186 | 119 | 0301 | 214 | 1 |
| 22 | 1301 | 0103 | 208 | 103 | 0603 | 222 | 15 |
| 23 | 1302 | 01021 | 210 | 103 | 0603 | 222 | 1 |
| 24 | 1302 | 01021 | 208 | 103 | 0604 | 220 | 1 |
| 25 | 1302 | 01021 | 210 | 103 | 0604 | 214 | 1 |
| 26 | 1302 | 01021 | 210 | 103 | 0604 | 220 | 8 |
| 27 | 1302 | 01021 | 210 | 103 | 0609 | 222 | 3 |
| 28 | 1401 | 0104 | 200 | 107 | 05031 | 218 | 8 |
| 29 | 0701 | 0201 | 212 | 121 | 0202 | 214 | 1 |
| 30 | 0701 | 0201 | 218 | 113 | 0202 | 214 | 7 |
| 31 | 0701 | 0201 | 218 | 117 | 0202 | 214 | 2 |
| 32 | 0701 | 0201 | 218 | 121 | 0202 | 214 | 4 |
| 33 | 0701 | 0201 | 214 | 119 | 03032 | 214 | 5 |
| 34 | 0701 | 0201 | 214 | 121 | 03032 | 214 | 2 |
| 35 | 0801 | 0401 | 198 | 113 | 0402 | 194 | 7 |
| 36 | 0801 | 0401 | 198 | 117 | 0402 | 194 | 1 |
| 37 | 0901 | 0302 | 198 | 115 | 03032 | 214 | 1 |
| 38 | 0901 | 0302 | 198 | 117 | 03032 | 214 | 2 |
| 39 | 1001 | 0105 | 198 | 103 | 0501 | 226 | 4 |
| | | | | | | | 198 |

No. of H = number of haplotypes observed

TABLE 9

Haplotypes found in 95 New Guinean subjects

| No. | DRB1 | DQA1 | CAR II | CAR I | DQB1 | G51152 | No. of H |
|---|---|---|---|---|---|---|---|
| 1 | 1501 | 01021 | 200 | 103 | 0502 | 214 | 8 |
| 2 | 1501 | 01021 | 200 | 103 | 0602 | 220 | 28 |
| 3 | 1502 | 01021 | 200 | 107 | 06011 | 214 | 44 |
| 4 | 1502 | 01021 | 200 | 107 | 06011 | 218 | 1 |
| 5 | 1602 | 01022 | 202 | 103 | 0502 | 214 | 18 |
| 6 | 0405 | 0302 | 194 | 113 | 0401 | 226 | 8 |

TABLE 9-continued

Haplotypes found in 95 New Guinean subjects

| No. | DRB1 | DQA1 | CAR II | CAR I | DQB1 | G51152 | No. of H |
|---|---|---|---|---|---|---|---|
| 7 | 0405 | 0302 | 194 | 113 | 0402 | 226 | 2 |
| 8 | 0407 | 0301 | 194 | 113 | 0302 | 226 | 3 |
| 9 | 0410 | 0302 | 194 | 113 | 0402 | 226 | 1 |
| 10 | 1101 | 05013 | 188 | 121 | 0301 | 214 | 22 |
| 11 | 1101 | 05013 | 188 | 123 | 0301 | 214 | 8 |
| 12 | 1101 | 05013 | 188 | 125 | 0301 | 214 | 5 |
| 13 | 1104 | 05013 | 188 | 121 | 0301 | 214 | 2 |
| 14 | 1201 | 05013 | 186 | 117 | 0301 | 214 | 1 |
| 15 | 1201 | 05013 | 186 | 119 | 0301 | 214 | 1 |
| 16 | 1201 | 01022 | 202 | 103 | 0502 | 214 | 1 |
| 17 | 1202 | 0601 | 198 | 113 | 0301 | 192 | 1 |
| 18 | 1401 | 0104 | 200 | 103 | 0502 | 214 | 3 |
| 19 | 1407 | 0104 | 200 | 107 | 05031 | 218 | 7 |
| 20 | 1408 | 0104 | 200 | 107 | 05031 | 218 | 20 |
| 21 | 08032 | 0103 | 206 | 103 | 0502 | 214 | 1 |
| 22 | 08032 | 0103 | 206 | 107 | 06011 | 214 | 4 |
| 23 | 0901 | 0302 | 198 | 117 | 03032 | 214 | 1 |
| | | | | | | | 190 |

No. of H = number of haplotypes observed

TABLE 10

Predictability of HLA DQ alleles using CAR, CARII, and G51152 markers

| | Japanese | | | | Norwegean | | | | New Guinean | | | |
|---|---|---|---|---|---|---|---|---|---|---|---|---|
| | # alleles | # errors | % accuracy | FI | # alleles | # errors | % accuracy | FI | # alleles | # errors | % accuracy | FI |
| DQA1 | | | | | | | | | | | | |
| 0101 | 101 | 0 | 100 | | 18 | 0 | 100 | | 0 | 0 | 100 | |
| 01021 | 194 | 1 | 98.9 | | 40 | 0 | 100 | | 81 | 1 | 98.8 | |
| 01022 | 8 | 0 | 100 | | 0 | 0 | 100 | | 19 | 0 | 100 | |
| 0103 | 313 | 0 | 100 | | 15 | 0 | 100 | | 5 | 0 | 100 | |
| 0104 | 55 | 0 | 100 | | 8 | 0 | 100 | | 30 | 3 | 90 | |
| 0105 | 5 | 0 | 100 | | 4 | 0 | 100 | | 0 | 0 | 100 | |
| 0201 | 3 | 0 | 100 | | 21 | 0 | 100 | | 0 | 0 | 100 | |
| 0301 | 122 | 64 | 47.5 | 0302 | 23 | 0 | 100 | | 3 | 3 | 0 | 0302 |
| 0302 | 471 | 5 | 98.9 | | 18 | 1 | 94.4 | | 12 | 0 | 100 | |
| 0401 | 25 | 1 | 96 | | 8 | 0 | 100 | | 0 | 0 | 100 | |
| 05011 | 7 | 0 | 100 | | 26 | 0 | 100 | | 0 | 0 | 100 | |
| 05013 | 71 | 1 | 98.6 | | 17 | 0 | 100 | | 39 | 0 | 100 | |
| 0503 | 41 | 0 | 100 | | 0 | 0 | 100 | | 0 | 0 | 100 | |
| 0601 | 20 | 2 | 90 | | 0 | 0 | 100 | | 1 | 0 | 100 | |
| all DQA1 | 1436 | 74 | 94.85 | | 198 | 1 | 99.49 | | 190 | 7 | 96.32 | |
| DQB1 | | | | | | | | | | | | |
| 0201 | 7 | 0 | 100 | | 26 | 0 | 100 | | 0 | 0 | 100 | |
| 0202 | 3 | 0 | 100 | | 14 | 0 | 100 | | 0 | 0 | 100 | |
| 0301 | 151 | 3 | 98 | | 31 | 0 | 100 | | 40 | 0 | 100 | |
| 0302 | 136 | 65 | 52.2 | 0401 | 24 | 0 | 100 | | 3 | 3 | 0 | 0401 |
| 03032 | 229 | 1 | 99.6 | | 10 | 0 | 100 | | 1 | 0 | 100 | |
| 0401 | 190 | 5 | 97.4 | | 0 | 0 | 100 | | 8 | 0 | 100 | |
| 0402 | 44 | 27 | 38.6 | 0401 | 8 | 0 | 100 | | 3 | 3 | 0 | 0401 |
| 0501 | 106 | 0 | 100 | | 22 | 0 | 100 | | 0 | 0 | 100 | |
| 0502 | 27 | 0 | 100 | | 0 | 0 | 100 | | 31 | 0 | 100 | |
| 05031 | 37 | 0 | 100 | | 8 | 0 | 100 | | 27 | 0 | 100 | |
| 06011 | 307 | 0 | 100 | | 0 | 0 | 100 | | 49 | 1 | 98 | |
| 0602 | 91 | 0 | 100 | | 26 | 0 | 100 | | 28 | 0 | 100 | |
| 0603 | 7 | 0 | 100 | | 16 | 0 | 100 | | 0 | 0 | 100 | |
| 0604 | 92 | 0 | 100 | | 10 | 0 | 100 | | 0 | 0 | 100 | |
| 0609 | 9 | 0 | 100 | | 3 | 0 | 100 | | 0 | 0 | 100 | |
| all DQB1 | 1436 | 101 | 92.97 | | 198 | 0 | 100 | | 190 | 7 | 96.32 | |

FI = false inferences

TABLE 11

DQCAR allele frequencies in Japanese IDDM patients and Japanese, New Guinean and Caucasian controls

| DQCAR alleles | IDDM N = 95 | Japanese N = 718 | Chi square | New Guinean N = 95 | Chi square | Caucasian N = 99 | Chi square |
|---|---|---|---|---|---|---|---|
| 99 | 3(3%) | 7(1%) | | NF | | 25(25%) | $x^2 = 19.16(p < 0.0001)$ |
| 103 | 24(25%) | 305(42%) | $x^2 = 10.32(p < 0.01)$ | 53(56%) | $x^2 = 18.36(p < 0.001)$ | 65(66%) | $x^2 -31.86(p < 10^{-6})$ |
| 107 | 10(11%) | 299(42%) | $x^2 = 34.48(p < 10^{-7})$ | 62(65%) | $x^2 = 60.47(p < 10^{-10})$ | 9(9%) | |
| 109 | 1(1%) | 10(1%) | | NF | | NF | |
| 111 | 12(13%) | 73(10%) | | NF | | 21(21%) | |
| 113 | 37(40%) | 213(30%) | | 13(14%) | $x^2 = 15.6(p < 0.001)$ | 14(14%) | $x^2 = 15.39(p < 0.001)$ |
| 115 | 66(69%) | 254(35%) | $x^2 = 40.87(p < 10^{-8})$ | NF | | 1(1%) | $x^2 = 100.51(p < 10^{-10})$ |
| 117 | 11(12%) | 132(18%) | | 2(2%) | $x^2 = 6.69(\pi < 0.01)$ | 18(18%) | |
| 119 | NF | NF | | 1(1%) | | 8(8%) | $x^2 = 8.01(P < 0.01)$ |
| 121 | 1(1%) | 34(5%) | | 20(21%) | $x^2 = 19.33(p < 0.001)$ | 14(14%) | $x^2 = 11.64(p < 0.001)$ |
| 123 | | 8(1%) | | 8(8%) | | 1(1%) | |
| 125 | | NF | | 5(5%) | | 1(1%) | |
| 127 | | 1(0%) | | NF | | NF | |

NF = not found
IDDM = Insulin-Dependent Diabetes Mellitus

---

What is claimed is:

1. A method of HLA typing, comprising:
   (a) characterizing at least one multiallelic microsatellite marker in the HLA DQ/DR region of the human genome, comprising the steps of
      (i) providing a sample containing DNA from an individual;
      (ii) determining the allele length of at least one of DQCAR, DQCARII or G51152 in the HLA DQ/DR region of said DNA;
   (b) predicting the HLA type of the individual based on the allele length of at least one multiallelic microsatellite marker characterized in step (a).

2. The method of claim 1, wherein the characterized microsatellite marker is DQCAR and its length is determined using primers of SEQ ID NO. 1 and SEQ ID NO. 2 or primers having sequences fully complementary to SEQ ID NO. 1 and SEQ ID NO. 2.

3. The method of claim 1, wherein the characterized microsatellite marker is DQCARII and its length is determined using primers of SEQ ID NO. 4 and SEQ ID NO. 5 or primers having sequences fully complementary to SEQ ID NO. 4 and SEQ ID NO. 5.

4. The method of claim 1, wherein the characterized microsatellite marker is G51152 and its length is determined using primers of SEQ ID NO. 6 and SEQ ID NO. 7 or primers having sequences fully complementary to SEQ ID NO. 6 and SEQ ID NO. 7.

5. The method of claim 1, wherein the predicted HLA type is used for assessing the susceptibility of an individual to a disease that is associated with said predicted HLA type.

6. The method of claim 1, wherein the predicted HLA type is used for evaluating the suitability of a tissue or organ transplantation donor.

7. A kit for HLA typing comprising at least two oligonucleotide primers of
   (i) SEQ ID NO. 1 and SEQ ID NO. 2;
   (ii) SEQ ID NO. 4 and SEQ ID NO. 5;
   (iii) SEQ ID NO. 6 and SEQ ID NO. 7;
   (iv) nucleic acid sequences fully complementary to SEQ ID NO. 1 and SEQ ID NO. 2;
   (v) nucleic acid sequences complementary to SEQ ID NO. 4 and SEQ ID NO. 5; or
   (vi) nucleic acid sequences complementary to SEQ ID NO. 6 and SEQ ID NO. 7;
   which can amplify microsatellite loci in the HLA DQ/DR region of the human genome.

8. The kit of claim 7, wherein the oligonucleotide primers can amplify DQCAR and have the nucleic acid sequences SEQ ID NO. 1 and SEQ ID NO. 2, or nucleic acid sequences fully complementary to SEQ ID NO. 1 and SEQ ID NO. 2.

9. The kit of claim 7, wherein the oligonucleotide primers can amplify DQCARII and have the nucleic acid sequences SEQ ID NO. 4 and SEQ ID NO. 5, or nucleic acid sequences fully complementary to SEQ ID NO. 4 and SEQ ID NO. 5.

10. The kit of claim 7, wherein the oligonucleotide primers can amplify G51152 and have the nucleic acid sequences SEQ ID NO. 6 and SEQ ID NO. 7, or nucleic acid sequences fully complementary to SEQ ID NO. 6 and SEQ ID NO. 7.

11. A primer having the sequence of SEQ ID NO. 4, SEQ ID NO. 5, SEQ ID NO. 6, SEQ ID NO. 7, or the full complement of SEQ ID NO. 4, SEQ ID NO. 5, SEQ ID NO. 6, or SEQ ID NO. 7.

12. A primer consisting of 20 bases, wherein said 20 bases match a series of 20 continuous bases within a sequence of SEQ ID NO. 4, SEQ ID NO. 5, SEQ ID NO. 6, SEQ ID NO. 7, or the full complement of SEQ ID NO. 4, SEQ ID NO. 5, SEQ ID NO. 6, or SEQ ID NO. 7.

13. An oligonucleotide of less than about 50 bases comprising a DNA segment having the sequence of SEQ ID NO. 4, SEQ ID NO. 5, SEQ ID NO. 6, SEQ ID NO. 7, or the full complement of SEQ ID NO. 4, SEQ ID NO. 5, SEQ ID NO. 6, or SEQ ID NO. 7.

14. A method of screening the suitability of a donor for tissue or organ transplantation, comprising comparing the allele length of at least one multiallelic microsatellite marker of DQCAR, DQCARII or G51152 in the HLA DQ/DR region of the human genome from a prospective tissue or organ donor with the allele length of said marker from a prospective tissue or organ recipient.

15. The method of claim 14, wherein said comparing step comprises amplifying DQCAR using primers comprising SEQ ID NO. 1 and SEQ ID NO. 2, or nucleic acid sequences fully complementary to SEQ ID NO. 1 and SEQ ID NO. 2.

16. The method of claim 14, wherein said comparing step comprises amplifying DQCARII using primers comprising SEQ ID NO. 4 and SEQ ID NO. 5, or nucleic acid sequences fully complementary to SEQ ID NO. 4 and SEQ ID NO. 5.

17. The method of claim 14, wherein said comparing step comprises amplifying G51152 using primers comprising SEQ ID NO. 6 and SEQ ID NO. 7, or nucleic acid sequences fully complementary to SEQ ID NO. 6 and SEQ ID NO. 7.

* * * * *

UNITED STATES PATENT AND TRADEMARK OFFICE
CERTIFICATE OF CORRECTION

PATENT NO.    :    5,908,749
DATED         :    June 1, 1999
INVENTOR(S)   :    Mignot et al.

It is certified that error appears in the above-identified patent and that said Letters Patent is hereby corrected as shown below:

In claim 1, column 31, line 51, "DOCAR" should read "DQCAR".

In claim 14, column 34, line 6, "DOCAR" should read "DQCAR".

Signed and Sealed this

Twelfth Day of October, 1999

*Attest:*

Q. TODD DICKINSON

*Attesting Officer*     *Acting Commissioner of Patents and Trademarks*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (xi) SEQUENCE DESCRIPTION: SEQ ID NO:1:

GAAACATATA TTAACAGAGA CAGACAAA    28

(2) INFORMATION FOR SEQ ID NO:2:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (xi) SEQUENCE DESCRIPTION: SEQ ID NO:2:

CATTTCTCTT CCTTATCACT TCATA    25

(2) INFORMATION FOR SEQ ID NO:3:

(i) SEQUENCE CHARACTERISTICS:
    (A) LENGTH: 177 base pairs
    (B) TYPE: nucleic acid
    (C) STRANDEDNESS: double
    (D) TOPOLOGY: linear (xi) SEQUENCE DESCRIPTION: SEQ ID NO:3:

TCTAGAAACA TATATTAACA GAGACAGACA AACACACACA CACACACACA CACACACACA    60

CACACACACA CACACAGCAA GAGAGAGAGA TGAGATAATA TATGAAGTGA TAAGGAAGAG    120

AAATGCAGAA AAAATAGACG CAAAAGAACA CGAGATAGAA AAAATGCAGA TAAACAG    177

(2) INFORMATION FOR SEQ ID NO:4:

(i) SEQUENCE CHARACTERISTICS:

-continued

```
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:4:

TGATTCATAA GGCAAGAATC CAGCATATTG G                                        31

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:5:

GCACTATCAT TAAATTTGCT TTCCACAGTA C                                        31

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

GGTAAAATTC CTGACTGGCC                                                     20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

GACAGCTCTT CTTAACCTGC                                                     20
```